United States Patent
Weiβenbach et al.

(10) Patent No.: US 9,108,992 B2
(45) Date of Patent: Aug. 18, 2015

(54) CARBOXYL-FUNCTIONALIZED SILICON-CONTAINING PRECURSOR COMPOUND OF VARIOUS ORGANIC CARBOXYLIC ACIDS

(75) Inventors: Kerstin Weiβenbach, Bridgewater, NJ (US); Aristidis Ioannidis, Rheinfelden (DE); Bastian Bielawski, Rheinfelden (DE); Christian Springer, Rheinfelden (DE); Jaroslaw Monkiewicz, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 333 days.

(21) Appl. No.: 13/580,385

(22) PCT Filed: Dec. 28, 2010

(86) PCT No.: PCT/EP2010/070770
§ 371 (c)(1),
(2), (4) Date: Nov. 1, 2012

(87) PCT Pub. No.: WO2011/103940
PCT Pub. Date: Sep. 1, 2011

(65) Prior Publication Data
US 2013/0037744 A1   Feb. 14, 2013

(30) Foreign Application Priority Data

Feb. 25, 2010 (DE) .................. 10 2010 002 358

(51) Int. Cl.
*C08J 3/20* (2006.01)
*C07F 7/18* (2006.01)
*C08G 77/14* (2006.01)

(52) U.S. Cl.
CPC ............. *C07F 7/1896* (2013.01); *C07F 7/1812* (2013.01); *C07F 7/1816* (2013.01); *C07F 7/1836* (2013.01); *C08G 77/14* (2013.01)

(58) Field of Classification Search
CPC ...... C08L 25/02; C08L 43/04; C08L 2310/00
USPC .................. 523/351; 252/182.15, 182.14
See application file for complete search history.

(56) References Cited

U.S. PATENT DOCUMENTS

| | | | |
|---|---|---|---|
| 4,870,111 | A | 9/1989 | Donuiff et al. |
| 6,528,585 | B1 | 3/2003 | Standke et al. |
| 6,864,323 | B2 | 3/2005 | Schlosser et al. |
| 6,946,537 | B2 | 9/2005 | Krafczyk et al. |
| 7,781,520 | B2 | 8/2010 | Standke et al. |
| 2003/0018155 | A1 | 1/2003 | Krafczyk et al. |
| 2003/0134969 | A1 | 7/2003 | Schlosser et al. |
| 2008/0027161 | A1 | 1/2008 | Schlosser et al. |
| 2008/0187673 | A1 | 8/2008 | Standke et al. |
| 2011/0144277 | A1* | 6/2011 | Weissenbach et al. ....... 525/288 |
| 2011/0144278 | A1 | 6/2011 | Weissenbach et al. |
| 2011/0282024 | A1 | 11/2011 | Weissenbach et al. |
| 2012/0065302 | A1 | 3/2012 | Weissenbach et al. |
| 2012/0080637 | A1 | 4/2012 | Herzog et al. |

FOREIGN PATENT DOCUMENTS

| | | |
|---|---|---|
| DE | 198 48 351 | 4/2000 |
| EP | 0426073 | * 10/1990 |
| EP | 1 318 526 | 6/2003 |

OTHER PUBLICATIONS

International Search Report Issued May 20, 2011 in PCT/EP10/070770 Filed Dec. 28, 2010.

* cited by examiner

*Primary Examiner* — Hannah Pak
(74) *Attorney, Agent, or Firm* — Oblon, McClelland, Maier & Neustadt, L.L.P.

(57) ABSTRACT

The invention relates to a composition of a carboxyl-functionalized silicon-containing precursor compound of at least two different organic acids, said composition having two, three, or four carboxyl groups functionalized with various hydrocarbon groups according to formula I and/or II. Said carboxyl groups can be released as carboxylic acids and can be used as silane hydrolysis catalysts and/or silane condensation catalysts. The invention further relates to methods for producing the composition, to the use of the composition for cross-linking polymers, and to a formulation of the composition in the form of a masterbatch.

15 Claims, 1 Drawing Sheet

US 9,108,992 B2

Figure 1:
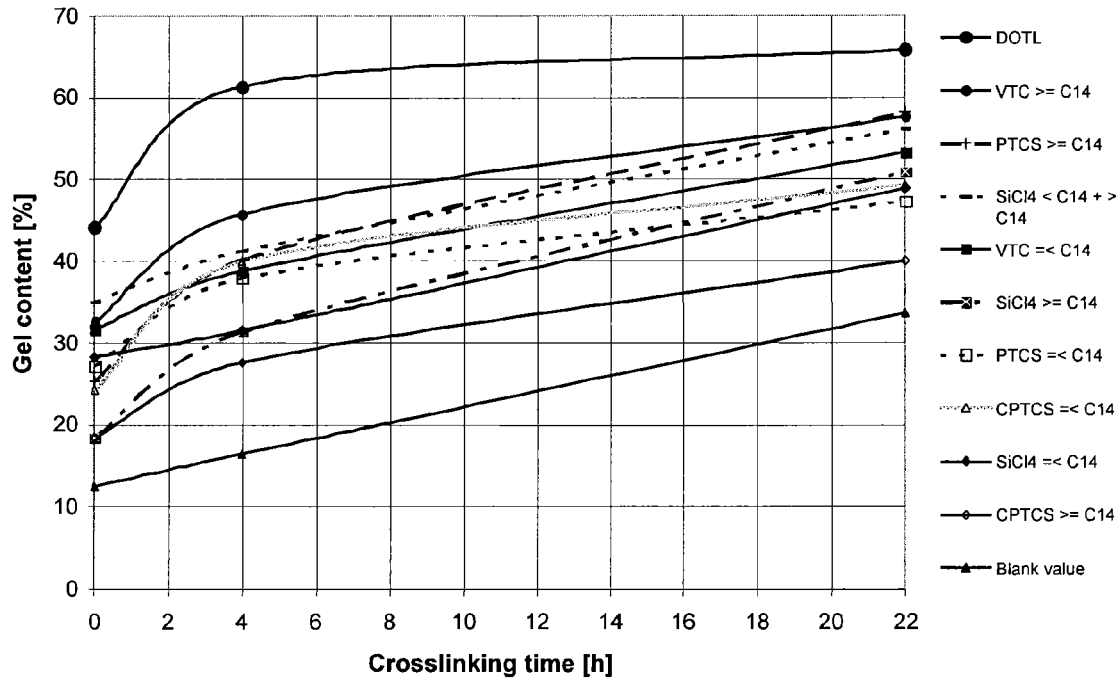

CARBOXYL-FUNCTIONALIZED SILICON-CONTAINING PRECURSOR COMPOUND OF VARIOUS ORGANIC CARBOXYLIC ACIDS

The invention relates to a composition of a carboxy-functionalized, silicon-containing precursor compound of at least two different organic acids, having two, three or four carboxyl groups functionalized with different hydrocarbon radicals, in accordance with formula I and/or II, which can be released as carboxylic acids and used as a silane hydrolysis catalyst and/or silane condensation catalyst. The invention further relates to processes for preparing them, to their use for the crosslinking of polymers, and also to a formulation thereof in the form of a masterbatch.

In the preparation of filled and unfilled polymer compounds, more particularly of polyethylene (PE) and its copolymers, it is known to crosslink silane-grafted or silane-copolymerized polyethylenes using organotin compounds or aromatic sulfonic acids (Borealis Ambicat®) as silanol condensation catalysts. A disadvantage of the organotin compounds is their significant toxicity, while the sulfonic acids attract attention for their pungent odor, which persists through all process stages right into the end product. As a result of reaction by-products, the polymer compounds crosslinked with sulfonic acids are generally unsuitable for use in the food sector or in the sector of drinking-water supply, as for example for the production of drinking-water pipes. Customary tin silanol condensation catalysts are dibutyltin dilaurate (DBTDL) and dioctyltin dilaurate (DOTL), which act as a catalyst via their coordination sphere.

In the preparation of moisture-crosslinkable polymers, it is known practice to graft silanes onto polymer chains in the presence of radical initiators and, after the shaping operation, to carry out moisture crosslinking in the presence of the aforementioned silane hydrolysis catalysts and/or silanol condensation catalysts. The moisture crosslinking of polymers with hydrolyzable unsaturated silanes is employed worldwide in the production of cables, pipes, foams, etc. Processes of this kind are known by the names of the Sioplas process (DE 19 63 571 C3, DE 21 51 270 C3, U.S. Pat. No. 3,646,155) and Monosil process (DE 25 54 525 C3, U.S. Pat. No. 4,117,195). Whereas with the Monosil process the crosslinking catalyst is added as early as during the first processing step, with the Sioplas process the crosslinking catalyst is not added until the subsequent, shaping step. Furthermore, vinyl-functional silanes can be copolymerized together with the monomers and/or prepolymers directly to form the base polymer, or can be coupled to polymers via grafting onto the polymer chains.

EP 207 627 discloses further tin-containing catalyst systems and copolymers modified therewith, based on the reaction of dibutyltin oxide with ethylene-acrylic acid copolymers. JP 58013613 uses $Sn(acetyl)_2$ as a catalyst, and JP 05162237 teaches the use of tin, zinc or cobalt carboxylates together with bound hydrocarbon groups as silanol condensation catalysts, such as dioctyltin maleate, monobutyltin oxide, dimethyloxybutyltin or dibutyltin diacetate. JP 3656545 uses zinc and aluminum soaps, such as zinc octylate, aluminum laurate, for crosslinking. For the crosslinking of silanes, JP 1042509 likewise discloses the use of organotin compounds, but also alkyltitanic esters based on titanium chelate compounds.

The fatty acid reaction products of functional trichlorosilanes have been common knowledge since the 1960s, especially as lubricant additives. DE 25 44 125 discloses the use of dimethyldicarboxylsilanes as a lubricant additive in the coating of magnetic tapes. In the absence of strong acids and bases, the compound is sufficiently stable toward a hydrolysis.

It is an object of the present invention to provide new, carboxy-functionalized, silicon-containing precursor compounds of organic acids that can be used as silane hydrolysis catalysts and/or silanol condensation catalysts, that do not have the stated disadvantages of the known catalysts from the prior art, and that can be dispersed or homogenized, and optionally polymerized, preferably with silane-grafted, silane-copolymerized polymers and/or monomers or prepolymers. A particular object is to custom-modify the properties of the precursor compounds, especially with regard to their solubility in organic media or their reactivity toward moisture or reactivity toward polymerizable compounds, or else the reactivity spectrum of the catalyst formed and also the aggregate state of the precursor compound, in order thereby to simplify their handling. Another object was to adjust the reactivity of unsaturated hydrocarbon-containing carboxysilanes as a functional comonomer or silanizing agent with respect to a polymerization reaction, e.g., with respect to thermoplastic base polymers or else monomers, such as ethylene.

The object is achieved by the composition of the invention, by the formulation of the masterbatch and by the processes of the invention and also by the use. Preferred embodiments are evident from the dependent claims and preferably from the description.

Surprisingly it has been found that the composition which comprises a hydrolyzable precursor compound of at least two different organic acids of the general formulae I and/or II can be custom-tailored in respect of its spectrum of properties to a given profile of requirements of the subsequent application through the correct selection of the carboxyl groups functionalized with different or various hydrocarbon radicals, preferably with $R^3$ is independently $R^{3a}$, $R^{3b}$, and $R^{3c}$, and optionally $R^{3d}$.

In this way, through the correct choice of, for example, fatty acids of the general formula IV that differ in length, comprising the fatty acids of the formulae IVa, IVb, IVc, and optionally IVd, it is possible, during the preparation of the precursor compound, to ensure that it is highly soluble in vinyltrimethoxysilane or vinyltriethoxysilane. Similarly, via the appropriate, correct choice of the different carboxylic acids of the formula IV, it is possible, in the preparation of the precursor compound of the formula I and/or II, to control the subsequent release of the reactive catalysts, i.e., of the acids of the formula IV, and also their reactivity in the polymerization processes.

The invention provides a composition comprising at least one carboxy-functionalized, silicon-containing precursor compound of organic acids, which comprises at least one carboxy-functionalized, silicon-containing precursor compound of two different organic acids, preferably of three or four different organic acids, more particularly suitable as a silane hydrolysis catalyst and/or silane condensation catalyst or as a catalyst precursor compound, and the carboxy-functionalized, silicon-containing precursor compound has at least two, preferably three to four, carboxyl groups functionalized with different hydrocarbon radicals, and corresponds to the general formula I and/or to an oligomeric siloxane, more particularly a dimer, trimer, low molecular mass oligo meric siloxane, derived from the compound of the general formula I in accordance with the idealized general formula II

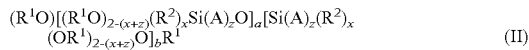

where in formulae I and II independently of one another z is 0, 1 or 2, x is 0, 1 or 2, with the proviso that (z+x) is less than or equal to (≤) 2, A independently at each occurrence in formulae I and II corresponds to an unsubstituted or substituted hydrocarbon group, more particularly to an unsubstituted or substituted linear, branched and/or cyclic alkyl, cycloalkenyl-alkylene, alkenyl, alkylaryl, arylalkylene, aryl, preferably phenyl; methacryloyloxyalkyl, acryloyloxyalkyl or halohydrocarbon group;

$R^1$ corresponds independently in formula I and in formula II, in each case independently of one another, to at least two different carbonyl-$R^3$ groups, where $R^3$ is selected from a substituted or unsubstituted hydrocarbon radical having 3 to 45 C atoms, preferably an unsubstituted hydrocarbon radical or hydrocarbon radical substituted by hydroxyl and/or carboxyl groups, preferably $R^1$ independently comprises $R^{1a}$=—(CO)$R^{3a}$, $R^{1b}$=—(CO)$R^{3b}$, and $R^{1c}$=—(CO)$R^{3c}$, and option ally $R^{1d}$=—(CO)$R^{3d}$, $R^2$ is independently in formulae I and II in each case independently of one another an unsubstituted linear, branched or cyclic alkyl group having 1 to 24 C atoms, more particularly having 1 to 16 C atoms, preferably having 1 to 8 C atoms, more preferably having 1 to 4 C atoms, or an aryl group, and in formula II, a is greater than or equal to (≥) 1 and b is greater than or equal to (≥) 1, more particularly in formula I and/or II, x is 0 or 1, z is 0 or 1, and (x+z) is less than or equal to (≤) 2, preferably x+y is less than or equal to (≤) 1, more preferably z=0 or 1 and x=0, such as preferably in olefinic carboxysilanes and/or tetracarboxysilanes of the formula I;

or it comprises mixtures of these compounds.

In accordance with the invention, the silicon-containing precursor compound of the formula I may be a carboxysilane, more particularly an olefinic carboxysilane, more particularly a tris-α-carboxysilane, and/or a tetracarboxysilane, more particularly a tetra-α-carboxysilane, having different carboxyl groups. The carboxysilane—the silicon-containing precursor compounds of different organic acids, more particularly different fatty acids—can be present in liquid phase and is therefore readily meterable. Alternatively it may be present, preferably, in solid phase and consequently becomes inert toward hydrolysis by atmospheric moisture. The olefinic carboxysilane of the formula I is, in accordance with the invention, an "all-in-one" package, being able to be copolymerized or grafted and at the same time being able to act as an adhesion promoter and/or silane hydrolysis catalyst and/or silanol condensation catalyst. The hydrolysis to give the organic acid takes place preferably only when heat and moisture are supplied.

The carboxy-functionalized, silicon-containing precursor compound is prepared by reaction, in accordance with reaction equations (a) or (b), of, for example but not exclusively, three or four organic acids of the general formula IV, encompassing the subgroups IVa, IVb, IVc, and IVd. Formula IV is $R^1$OH and the subgroup IVa=$R^{1a}$OH, IVb=$R^{1b}$OH, IVc=$R^{1c}$OH, IVd=$R^{1d}$OH.

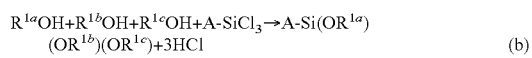

$R^1$ in formula I and/or II independently of one another corresponds to different carbonyl-$R^3$ groups, i.e., different —(CO)$R^3$ groups (—(C=O)—$R^3$), and so each $OR^1$ corresponds preferably to different —O(CO)$R^3$, such as, for example, —O(CO)$R^3$ comprises —O(CO)$R^{3a}$, —O(CO)$R^{3b}$, —O(CO)$R^{3c}$, —O(CO)$R^{3d}$, where each $R^3$ corresponds to an unsubstituted or substituted hydrocarbon radical (HC radical), more particularly having 1 to 45 C atoms, preferably having 3 to 45 C atoms, more particularly having 7 to 45 C atoms, better 7 to 26 C atoms or 7 to 22, preferably having 8 to 45 C atoms, preferably having 8 to 22 C atoms, more preferably having 8 to 18 C atoms, preferentially having 8 to 16 C atoms or else 8 to 13 or 14 C atoms, more particularly a linear, branched and/or cyclic unsubstituted and/or substituted hydrocarbon radical, very preferably a hydrocarbon radical of a natural or synthetic fatty acid; more particularly, each $R^3$ in $R^1$ independently of any other is a saturated HC radical with —$C_nH_{2n+1}$ where n=4 to 45, such as —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{37}$, $C_{19}H_{39}$, —$C_{20}H_{41}$, —$C_{21}H_{43}$, —$C_{22}H_{45}$, —$C_{23}H_{47}$, —$C_{24}H_{49}$, —$C_{25}H_{51}$, —$C_{26}H_{53}$, $C_{27}H_{55}$, —$C_{28}H_{57}$, —$C_{29}H_{59}$, or else, preferably, an unsaturated HC radical, such as, for example, —$C_{10}H_{19}$, —$C_{15}H_{29}$, —$C_{17}H_{33}$, —$C_{17}H_{33}$, —$C_{19}H_{37}$, —$C_{21}H_{41}$, —$C_{21}H_{41}$, —$C_{21}H_{41}$, —$C_{23}H_{45}$, —$C_{17}H_{31}$, —$C_{17}H_{29}$, —$C_{17}H_{29}$, —$C_{19}H_{31}$, —$C_{19}H_{29}$, —$C_{21}H_{33}$ and/or —$C_{21}H_{31}$. The shorter-chain HC radicals $R^3$, such as —$C_4H_9$, —$C_3H_7$, —$C_2H_5$, —$CH_3$ (acetyl) and/or $R^3$=H (formyl) may likewise be used in the composition. The general formula IV with $R^1$OH therefore encompasses the different acids of subgroup IVa $R^{1a}$OH=HO(CO)$R^{3a}$, IVb $R^{1b}$OH=HO(CO)$R^{3b}$, IVc $R^{1c}$OH=HO(CO)$R^{3c}$, IVd $R^{1d}$OH=HO(CO)$R^{3d}$.

In view of the low hydrophobicity of the HC radicals, however, the composition is based generally on compounds of the formula I and/or II in which different radicals $R^1$ each have a carbonyl-$R^3$ group, selected from the group $R^3$, with an unsubstituted or substituted hydrocarbon radical having 3 to 45 C atoms, having 7 to 45 C atoms, more particularly having 7 to 26 C atoms, preferably having 7 to 22 C atoms, more preferably having 7 to 14 C atoms or preferentially having 7 to 13 C atoms.

Carbonyl-$R^3$ groups, independently encompassing carbonyl —$R^{3a\ to\ d}$, are understood to be the acid radicals of the organic carboxylic acids, such as $R^3$—(CO)—, which are bonded as different carboxyl groups in accordance with the formulae I and/or II to the silicon as per Si—$OR^1$, as set out above. Generally speaking, the carboxyl groups functionalized with different hydrocarbon radicals (—$OR^1$ with $R^1$=—(CO)—$R^3$), i.e., the acid radicals of the formula I and/or II, may be obtained from naturally occurring or synthetic fatty acids, such as the saturated fatty acids valeric acid (pentanoic acid, $R^3$=$C_4H_9$), caproic acid (hexanoic acid, $R^3$=$C_5H_{11}$), enanthic acid (heptanoic acid, $R^3$=$C_6H_{13}$), caprylic acid (octanoic acid, $R^3$=$C_7H_{15}$), pelargonic acid (nonanoic acid $R^3$=$C_8H_{17}$), capric acid (decanoic acid, $R^3$=$C_9H_{19}$), lauric acid (dodecanoic acid $R^3$=$C_{11}H_{23}$), undecanoic acid ($R^3$=$C_{10}H_{21}$), tridecanoic acid ($R^3$=$C_{12}H_{25}$), myristic acid (tetradecanoic acid, $R^3$=$C_{13}H_{27}$), pentadecanoic acid, $R^3$=$C_{14}H_{29}$) palmitic acid (hexadecanoic acid, $R^3$=$C_{15}H_{31}$), margaric acid (heptadecanoic acid, $R^3$=$C_{16}H_{33}$), stearic acid (octadecanoic acid, $R^3$=$C_{17}H_{35}$), nonadecanedecanoic acid, ($R^3$=$C_{18}H_{37}$), arachidic acid (eicosanoic/icosanoic acid, $R^3$=$C_{19}H_{39}$), behenic acid (docosanoic acid, $R^3$=$C_{21}H_{43}$), lignoceric acid (tetracosanoic acid, $R^3$=$C_{23}H_{47}$), cerotic acid (hexacosanoic acid, $R^3$=$C_{20}H_{51}$), montanic acid (octacosanoic acid, $R^3=C_{27}H_{55}$) and/or melissic acid (triacontanoic acid, $R^3=C_{29}H_{59}$), but also the short-chain unsaturated fatty acids, such as valeric acid (pentanoic acid, $R^3=C_4H_9$), butyric acid (butanoic acid, $R^3=C_3H_7$), propionic acid (propanoic acid, $R^3=C_2H_5$), acetic acid ($R^3=CH_3$) and/or formic acid ($R^3=H$), and may be used as silicon-containing precursor compound of the formula I and/or II, more particularly as otherwise purely organic silanol hydrolysis and/or condensation catalysts.

The invention also provides compositions comprising compounds of the formula I and/or II obtainable from the reaction of a compound of formula III with two, three or four different fatty acids, more particularly of the formulae IVa, IVb, IVc, and optionally IVd, selected from caprylic acid, oleic acid, lauric acid, capric acid, stearic acid, palmitic acid, behenic acid and/or myristic acid, for preparing the compound of the formula I and/or II, with particularly preferred fatty acids being selected from caprylic acid, lauric acid, capric acid, behenic acid and/or myristic acid.

The corresponding carboxysilane compounds having different carboxyl groups show on average a better crosslinking than the free acids in the case, for example, of crosslinking reactions of methoxysilane-grafted PE-HD polymers—see Working examples. All in all, the solid carboxysilanes, with carboxyl radicals of bigger than 14 C atoms, show significantly better crosslinking than the liquid carboxysilanes, with carboxyl radicals smaller than 14 C atoms, and crosslink much better than the carboxysilanes with 3 identical carboxyl radicals. Without being tied to one theory, it is assumed that, when three or four of the carboxyl groups in the carboxysilane have more than 14 C atoms, i.e., 15 C atoms and more, the carboxysilanes prepared are solid, even if one of these carboxyl groups has 14 C atoms or fewer (less than 13 C atoms). Moreover, a higher degree of compatibility with the nonpolar polymer matrix is generated, and this is manifested in better distribution and hence, in association with this, a better activity on the part of the catalyst.

In accordance with particularly preferred embodiments of the invention, it is possible in each case in formula I and/or II for A to be a linear, branched or cyclic alkyl-, alkenyl-, aryl-, alkylaryl-, aryl-alkylene-, cycloalkenyl-alkylene-, haloalkyl- and/or acryloyloxyalkyl-functional group, more particularly a linear, branched and/or cyclic alkyl group or cycloalkenyl-alkylene group having 1 to 18 C atoms and/or in each case a linear, branched and/or cyclic arylalkylene, haloalkyl, alkenyl, alkynyl and/or acryloyloxyalkyl group having in each case 1 to 18 C atoms and/or an aryl group having 6, 12 or 14 C atoms and/or an isoalkyl group having 1 to 18 C atoms, a cycloalkyl group having 1 to 18 C atoms, such as a cyclohexyl group, 3-methacryloyloxypropyl group, a 3-acryloyloxypropyl group, fluoroalkyl group, vinyl group, allyl group; with particular preference A is an alkenyl group, more preferably a vinyl group, or an alkyl group, more preferably a propyl or else a haloalkyl group, such as, preferably, a 3-chloropropyl group. Likewise preferably A is a cycloalkenyl-alkylene group having 1 to 16 C atoms, preferably cyclohexenyl-alkylene having 1 to 8 C atoms in the divalent alkylene group, more preferably a cyclohexenyl-ethylene group, with further preference a 3-cyclohexenyl-ethylene group or else a 2-cyclohexenyl-ethylene or 1-cyclohexenyl-ethylene group; corresponding cyclohexenyl-propylene groups are also preferred such as cyclohexadienyl-alkylene groups having 1 to 4 C atoms in the divalent alkylene group.

Likewise A is preferably, independently at each occurrence in formula I and/or II, a monovalent olefin group, such as more particularly $C_6H_9$—$(CH_2)_2$—, preferably 3-$C_6H_9$—$(CH_2)_2$—, 2-$C_6H_9$—$(CH_2)_2$—, 1-$C_6H_9$—$(CH_2)_2$—, or else $C_6H_8$—$(CH_2)_2$—, more particularly 1,3-$C_6$—$H_8$—$(CH_2)_2$— or 2,4-$C_6H_8$—$(CH_2)_2$— or $R^9)_2C=C(R^9)$-$M_k$-, in which $R^9$ is identical or different and $R^9$ is a hydrogen atom or a methyl group or a phenyl group, the group M represents a group from the series —$CH_2$—, —$(CH_2)_2$—, —$(CH_2)_3$—, —O(O)C$(CH_2)_3$— or —C(O)O—$(CH_2)_3$—, k is 0 or 1, such as vinyl, allyl, 3-methacryloyloxypropyl and/or acryloyloxypropyl, n-3-pentenyl, n-4-butenyl or isoprenyl, 3-pentenyl, hexenyl, -alkylene-cyclohexenyl having 1 to 8 C atoms in the divalent alkylene group, preferably 1 to 4 C atoms; -ethylene-cyclohexenyl, cyclohexenyl, cyclohexadiene, -ethylene-cyclohexadiene, terpenyl, squalanyl, squalenyl, polyterpenyl, betulaprenoxy, cis/trans-polyisoprenyl, or $R^8$—$F_g$—$[C(R^8)=C(R^8)$—$C(R^8)=C(R^8)]_r$—$F_g$—, in which $R^8$ radicals are identical or different and $R^6$ is a hydrogen atom or an alkyl group having 1 to 3 C atoms or an aryl group or an aralkyl group, preferably a methyl group or a phenyl group, groups F are identical or different and F represents a group from the series —$CH_2$—, —$(CH_2)_2$—, —$(CH_2)_3$—, —O(O)C$(CH_2)_3$— or —C(O)O—$(CH_2)_3$—, r is 1 to 100, more particularly 1 or 2, and g is 0 or 1, comprises.

Preferably there is no longer any alcohol released when at least one silicon-containing precursor compound of different organic acids, preferably of the general formula I with z=1 or 2 and/or with z=0 and different $OR^1$ encompassing —$OR^{1a}$=—O(CO)$R^{3a}$; —$OR^{1b}$=—O(CO)$R^{3b}$; —$OR^{1c}$=—O(CO)$R^{3c}$ and/or —$OR^{1d}$=—O(CO)$R^{3d}$ with unsaturated carboxylate radicals, corresponds in particular to a tetracarboxysilane, is grafted onto a base polymer or is copolymerized with a monomer and/or prepolymer of the base polymer, optionally in the presence of a radical initiator, or is mixed with a corresponding carboxyl-substituted silane-grafted base polymer and optionally after shaping, preferably with supply of heat, brings about, as a catalyst, the crosslinking in the presence of moisture. The grafting or copolymerizing may additionally take place in the presence of an organofunctional silane compound, such as an unsaturated alkoxysilane of the general formula V $((B)_bSiR^4_c(OR^5)_{3-d-c})$, as defined below.

In formula I preferably z=1 and x=0 or z=0 and x=1 for the tricarboxysilanes and/or for the tetracarboxysilanes z=0 and x=0. Likewise preferred are the corresponding oligomeric siloxanes of the formula II.

Preference is given accordingly to silanes of the formula I and/or II that are based on and/or release different carboxylic acids, and which have two, three or four different carboxylic acids selected from capric acid, myristic acid, caprylic acid, oleic acid, stearic acid, palmitic acid, and lauric acid.

Particularly preferred compositions comprising precursor compounds of the formula I and/or II or else the precursor compound of the formula I or II as such or mixtures thereof in which (i) in each case independently of one another in formula I and/or II z is 1 and x is 0 and A corresponds to a linear, branched or cyclic alkyl, alkenyl, haloalkyl, cycloalkenyl-alkylene, more particularly cyclohexenyl-alkylene or alkenyl group having 1 to 8 C atoms and $R^1$ independently at each occurrence corresponds to two or three different carbonyl-$R^3$ groups (—(C=O)$R^3$ groups), preferably corresponds to three different carbonyl-$R^3$ groups, i.e., —(C=O)$R^3$ is —(C=O)$R^{3a\ to\ c}$, where independently $R^3$ is selected from an unsubstituted hydrocarbon radical having 3 to 45 C atoms, preferably an alkyl or alkenyl radical, more particularly having 7 to 45 C atoms, preferably 7 to 26 C atoms, or (ii) in each case independently of one another in formula I and/or II z is 0 and x is 0 and $R^1$ independently at each occurrence corresponds to two, three or four different carbonyl-$R^3$ groups (—(C=O)$R^3$ groups), i.e., —(C=O)$R^1$ is —(C=O)$R^{3a\ to\ d}$, where $R^3$ is selected from an unsubstituted hydrocarbon radical having 3 to 45 C atoms, preferably an alkyl or alkenyl radical, more particularly having 7 to 45 C atoms, more preferably having 7 to 26 C atoms.

Surprisingly it has been found that the aggregate state of the composition or else of the precursor compound of the formula I and/or II or mixtures thereof can be adjusted if specifically in each case independently of one another in formula I and/or II $R^1$ independently at each occurrence corresponds to at least two different carbonyl-$R^3$ groups (—(C=O)$R^{3a\ to\ c\ or\ d}$ groups), preferably three or four, where in the different carbonyl-$R^3$ groups (a) independently of one another at least one first $R^3$ radical is selected from an unsubstituted hydrocarbon radical having 3 to 14 C atoms, more particularly having 7 to 14 C atoms, preferably 8 to 14 C atoms, more preferably having 9 to 13 or 9 to 14 C atoms, preferably alkyl or alkenyl radicals, and (b) independently of one another at least one further $R^3$ radical is independently selected from an unsubstituted hydrocarbon radical having 15 to 45 C atoms, more particularly 15 to 26 C atoms, preferably 15 to 20 C atoms, preferably alkyl or alkenyl radicals.

Preferred aforementioned hydrocarbon radicals $R^3$ of the carbonyl-$R^3$ groups (—(C=O)$R^3$ groups) correspond to alkyl or alkenyl radicals having the stated number of C atoms.

The carboxy-functionalized, silicon-containing precursor compounds of the formula I and/or II are preferably based on different fatty acid radicals, i.e., more particularly, on the reaction of a halosilane of the formula III with different fatty acids ($R^1$OH=$R^{3a}$OH, $R^{1b}$OH, $R^{1c}$OH and/or $R^{1d}$OH), and each have a hydrophobic HC radical which is sufficiently hydrophobic, does not have any unpleasant odor after release, and does not bleed from the polymers prepared. An HC radical is sufficiently hydrophobic if the respective acid can be dispersed in the polymer or in a monomer or prepolymer. Particularly preferred acid radicals (—O$R^1$) in the formulae I and/or II result from the following acids, such as capric acid, lauric acid, myristic acid, stearic acid, palmitic acid and/or behenic acid.

Likewise with preference it is possible for the different naturally occurring or synthetic unsaturated fatty acids, i.e., at least one $R^3$ group in the different —O$R^1$ in formula I and/or II corresponds with $R^1$=—(CO)—$R^3$ equal to $R^{1a\ to\ d}$=—(CO)—$R^{3a\ to\ d}$, with $R^3$ an alkenyl group, including cycloalkenyl-alkylene groups, to be reacted to give the precursor compounds of the formula I and/or II, and so the compound of the formula I and/or II may have at least one of the following radicals $R^3$ in —O$R^1$=—O(CO)—$R^3$. These compounds of the formula I and/or II may fulfill two functions at the same time; on the one hand, they serve as silane hydrolysis catalyst and/or as silanol condensation catalyst and/or precursors thereof, and by virtue of their unsaturated hydrocarbon radicals ($R^3$) they are able to participate directly in radical polymerization. Preferred unsaturated fatty acids are sorbic acid ($R^3$=$C_5H_7$), undecylenic acid ($R^3$=$C_{10}H_{19}$) palmitoleic acid ($R^3$=$C_{15}H_{29}$) oleic acid ($R^3$=$C_{17}H_{33}$), elaidic acid ($R^3$=$C_{17}H_{33}$), vaccenic acid ($R^3$=$C_{17}H_{33}$), icosenoic acid ($R^3$=$C_{21}H_{41}$), cetoleic acid ($R^3$=$C_{21}H_{41}$), erucic acid ($R^3$=$C_{21}H_{41}$), nervonic acid ($R^3$=$C_{23}H_{45}$) linoleic acid ($R^3$=$C_{17}H_{31}$), alpha-linolenic acid ($R^3$=$C_{17}H_{29}$), gamma-linolenic acid ($R^3$=$C_{17}H_{29}$) arachidonic acid ($R^3$=$C_{19}H_{31}$), timnodonic acid ($R^3$=$C_{19}H_{29}$), clupanodonic acid ($R^3$=$C_{21}H_{33}$), ricinoleic acid (12-hydroxy-9-octadecenoic acid, $R^3$=$C_{17}H_{33}$O) and/or cervonic acid ($R^3$=$C_{23}H_{31}$). Particularly preferred are precursor compounds of the formula I and/or II containing at least one radical of oleic acid ($R^3$=$C_{17}H_{33}$).

Particularly preferred compositions comprise, more particularly in addition to the aforementioned features, at least one carboxy-functionalized, silicon-containing precursor compound of the formula I (iii) where z is 1 and A is $H_3C(CH_2)_2$—, $H_2C$=$CH_2$—, $ClCH_2(CH_2)_2$—, cyclohexenyl-alkylene- and/or cyclohexadienyl-alkylene- having 1 to 8 C atoms in the divalent alkylene group, such as $C_6H_9$—$(CH_2)_2$—, preferably 3-$C_6H_9$—$(CH_2)_2$—, 2-$C_6H_9$—$(CH_2)_2$—, 1-$C_6H_9$—$(CH_2)_2$—; or $C_6H_8$—$(CH_2)_2$—, 1,3-$C_6H_8$—$(CH_2)_2$— or 2,4-$C_6H_8$—$(CH_2)_2$— and O$R^1$ in formula I with two or three different radicals $R^1$ selected from $R^1$ ($R^1$=$R^{1a\ to\ c}$) selected from —$COC_7H_{15}$, —$COC_9H_{19}$, —$COC_{11}H_{23}$, —$COC_{13}H_{27}$, —$COC_{18}H_{31}$, —$COC_{17}H_{35}$ and —$COC_{21}H_{43}$, or (iv) where z is 0 and O$R^1$ in formula I with two, three or four different radicals $R^1$ ($R^1$=$R^{1a\ to\ d}$) selected from —$COC_7H_{15}$, —$COC_9H_{19}$, —$COC_{11}H_{23}$, —$COC_{13}H_{27}$, —$COC_{15}H_{31}$, —$COC_{17}H_{35}$ and —$COC_{21}H_{43}$, and optionally oligomeric compounds formed from the precursor compounds of the formula I in accordance with the idealized formula II, more particularly with a as 1 and b as 1, or a mixture of these.

Examples thereof are in particular with A as alkyl group, such as $H_3C(CH_2)_2$—, ($H_9C_4$)—, ($H_{17}C_8$)—, ($H_{33}C_{16}$)—; alkenyl group, such as $H_2C$=$CH_2$—, cycloalkenyl-alkylene- having 1 to 16 C atoms, more particularly cyclohexenyl-alkylene- and/or cyclohexadienyl-alkylene- having in each case 1 to 8 C atoms in the divalent alkylene group, such as more particularly $C_6H_9$—$(CH_2)_2$—, 3-$C_6H_9$—$(CH_2)_2$—, 2-$C_6H_9$—$(CH_2)_2$—, 1-$C_6H_9$—$(CH_2)_2$—, $C_6H_8$—$(CH_2)_2$—, 1,3-$C_6H_8$—$(CH_2)_2$— or 2,4-$C_6H_8$—$(CH_2)_2$—, more particularly -ethylene-2-cyclohex-3-enyl or isomers with a different position of the double bond, and/or haloalkyl group, such as $ClCH_2(CH_2)_2$—:

A-Si(OCO$C_7H_{15}$)$_p$(OCO$C_{11}H_{23}$)$_p$(OCO$C_{13}H_{27}$)$_p$(myristyl-, lauryl-, capryl-)

A-Si(OCO$C_{13}H_{27}$)$_p$(OCO$C_{15}H_{31}$)$_p$(OCO$C_{17}H_{35}$)$_p$(myristyl-, palmityl-, stearyl-)

($H_{19}C_9$OCO)$_p$(A)  Si(OCO$C_7H_{15}$)$_p$(OCO$C_{11}H_{23}$)$_p$(OCO$C_{13}H_{27}$)$_p$, (caprinyl-, myristyl-, lauryl-, capryl-);

($H_{43}C_{21}$OCO)$_p$(A)  Si(OCO$C_{13}H_{27}$)$_p$(OCO$C_{15}H_{31}$)$_p$(OCO$C_{17}H_{35}$)$_p$(behenyl-, myristyl-, palmityl-, stearyl-);

($H_{19}C_9$OCO)$_p$(A)  Si(OCO$C_7H_{15}$)$_p$(OCO$C_{11}H_{23}$)$_p$(OCO$C_{13}H_{27}$)$_p$, ($H_{19}C_9$OCO)$_p$Si(OCO$C_7H_{15}$)$_p$(OCO$C_{11}H_{23}$)$_p$(OCO$C_{13}H_{27}$)$_p$, (caprinyl-, myristyl-, lauryl-, capryl);

($H_{43}C_{21}$OCO)$_p$Si(OCO$C_{13}H_{27}$)$_p$(OCO$C_{15}H_{31}$)$_p$(OCO$C_{17}H_{35}$)$_p$ with in each case p being 0, 1, 2 or 3, with the proviso that at least in the case of two different fatty acid radicals, p is 1, and the sum of all of the p per silicon compound is 3 in Si-A substituted precursor compounds, and the sum of all of the p is 4 in tetra-carboxy-functionalized precursor compounds of the formula I, and also, optionally, corresponding oligomeric compounds of the precursor compounds of the formula I in accordance with the idealized formula II, more particularly with a as 1 and b as 1, or a mixture of these.

Particularly preferred carboxy-functionalized, silicon-containing precursor compounds of the formula I, though not restricted to these, are selected from

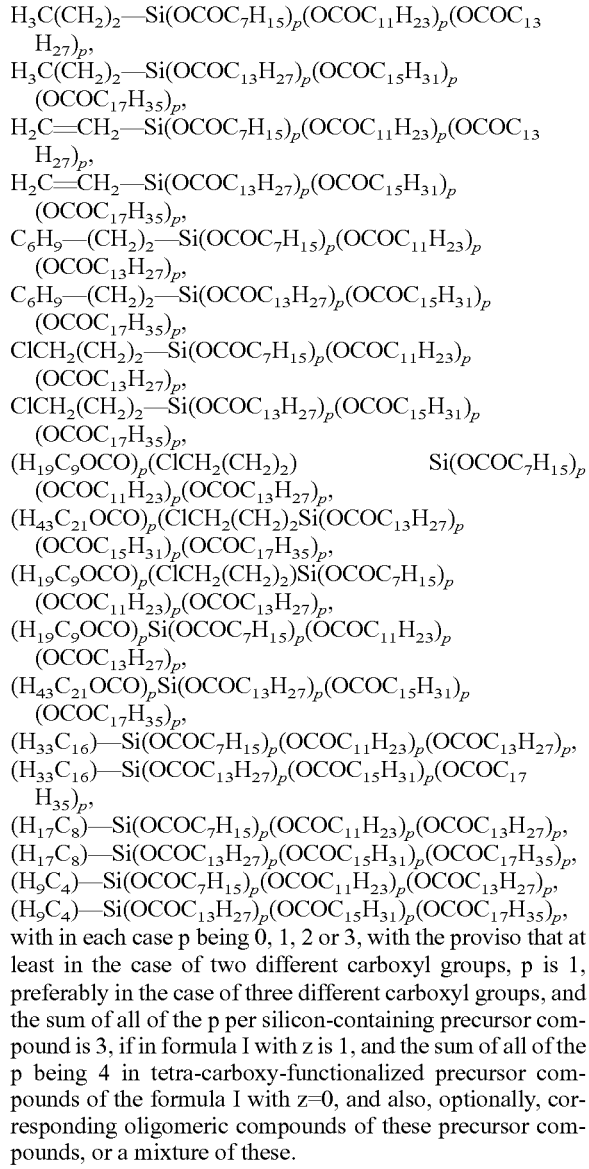

with in each case p being 0, 1, 2 or 3, with the proviso that at least in the case of two different carboxyl groups, p is 1, preferably in the case of three different carboxyl groups, and the sum of all of the p per silicon-containing precursor compound is 3, if in formula I with z is 1, and the sum of all of the p being 4 in tetra-carboxy-functionalized precursor compounds of the formula I with z=0, and also, optionally, corresponding oligomeric compounds of these precursor compounds, or a mixture of these.

Further useful acids from which the precursor compounds of the formula I and/or II with $R^3$—COO and/or $R^1$O may be prepared are glutaric acid, lactic acid ($R^1$ as $(CH_3)(HO)CH$—), citric acid ($R^1$ as $HOOCCH_2C(COOH)(OH)CH_2$—), vulpinic acid, terephthalic acid, gluconic acid, adipic acid, in which case it is also possible for all of the carboxyl groups to be Si-functionalized, benzoic acid ($R^1$ as phenyl), nicotinic acid (vitamin B3, B5). It is, however, also possible to use the natural or else synthetic amino acids, and so $R^1$ corresponds to corresponding radicals, such as starting from tryptophan, L-arginine, L-histidine, L-phenylalanine, L-leucine, where L-leucine can be used with preference. Correspondingly it is also possible to use the corresponding D-amino acids, or mixtures of L- and D-amino acids, or an acid, such as $D[(CH_2)_d)COOH]_3$ with D=N, P and d independently=1 to 12, preferably 1, 2, 3, 4, 5, or 6, in which independently the hydroxyl group of each carboxylic acid function may be Si-functionalized.

Hence it is also possible for corresponding compounds of the formula I and/or II based on radicals of these acids to be used as silane hydrolysis catalyst and/or silanol condensation catalyst.

The silicon-containing precursor compound of an organic acid is active more particularly in hydrolyzed form as silane hydrolysis and/or silanol condensation catalyst, via the organic acid released, and even in hydrolyzed or unhydrolyzed form is suitable for grafting on a polymer and/or copolymerization with a base polymer, polymer/monomer or prepolymer, or for crosslinking, for example as an adhesion promoter. In hydrolyzed form, the silanol compound formed contributes, in the case of condensation, to crosslinking by means of Si—O—Si siloxane bridges and/or Si—O substrate or Si—O carrier material formed. This crosslinking may take place with other silanols, siloxanes or, generally, with functional groups that are suitable for crosslinking on substrates, fillers and/or carrier materials. Preferred fillers and/or carrier materials are therefore aluminum hydroxides, magnesium hydroxides, fumed silica, precipitated silica, silicates, and also others of the carrier materials and fillers specified below.

Particularly suitable alkyl groups $R^2$ are linear, branched or cyclic alkyl groups having 1 to 24 C atoms, preferably having 1 to 18 C atoms, more preferably having 1 to 4 C atoms in the case of alkyl groups. Particularly suitable as alkyl group $R^2$ are ethyl, n-propyl and/or isopropyl groups. Particularly suitable substituted alkyl groups are halogenated hydrocarbons, such as 3-halopropyl, as for example 3-chloropropyl or 3-bromopropyl groups, which where appropriate are amenable to nucleophilic substitution or else may be employed in PVC. A suitable aryl group is phenyl or benzyl.

Hence preference is also given to silicon-containing precursor compounds of an organic acid of the general formula I and/or II that are based on alkyl-substituted di- or tricarboxysilanes with z=0 and x=1 or 2, and on different carboxylic acids, or releases a silanol and different carboxylic acids. Examples thereof are methyl-, dimethyl-, ethyl- or methylethyl-substituted carboxysilanes of the formula I, preferably based on two or three different carboxylic acids selected from capric acid, myristic acid, caprylic acid, oleic acid, stearic acid, palmitic acid, and lauric acid.

In order to allow ease of handling with regard to the metering of the composition comprising substantially carboxy-functionalized, silicon-containing precursor compounds of the formula I and/or II, it is possible, in accordance with one alternative, for liquid precursor compounds to be preferred, more particularly those which are liquid in the range from about 10° C. to 80° C., more particularly between 10 to 60° C., preferably between 10 to 40° C., more preferably between 10 to 35° C., in each case under standard pressure (around 1013 hPa).

In accordance with another preferred alternative, the composition comprising at least one precursor compound of the formula I and/or II may be applied to a carrier material, encapsulated and/or incorporated into a carrier material, the carrier material being more particularly a mineral material or a thermoplastic base polymer, a silane-grafted base polymer, a silane-copolymerized base polymer, a monomer of this base polymer, a prepolymer of these base polymers, and/or mixtures of these. Mineral materials contemplated, as fillers, for example, include in particular the following:

Preferred carrier materials and/or fillers are, accordingly, metal hydroxides with a stoichiometric proportion or, in their various dehydration stages, with a substoichiometric proportion of hydroxyl groups, through to oxides having comparatively few residual hydroxyl groups which, however, are detectable by DRIFT-IR spectroscopy. Examples of suitable carrier materials or fillers are aluminum trihydroxide (ATH), aluminum oxide hydroxide (AlOOH.aq), magnesium dihydroxide (MDH), brucite, huntite, hydromagnesite, mica, and montmorillonite. As filler it is additionally possible to use calcium carbonate, talc, and also glass fibers. Furthermore, so-called "char formers", such as ammonium polyphosphate, stannates, borates, talc, or those in combination with other fillers, may be used.

Furthermore, the composition may include other adjuvants, such as, for example, titanium oxide ($TiO_2$), talc, clay, quartz, kaolin, bentonite, calcium carbonate (chalk, dolomite), or else colors, pigments, talc, carbon black, $SiO_2$, precipitated silica, fumed silca, aluminum oxides, such as alpha- and/or gamma-aluminum oxide, aluminum oxide hydroxides, boehmite, barite, barium sulfate, lime, silicates, aluminates, aluminum silicates and/or ZnO or mixtures of these. The carrier materials or adjuvants, such as pigments, fillers, are preferably in powder, particulate, porous, swellable or optionally foam form.

Furthermore, high dispersibility or homogenizability, through to good solubility, of the composition comprising the carboxy-functionalized precursor compound of the formula I and/or II is desirable, especially in organofunctional silanes, organo-functional siloxanes, preferably also in silane-grafted, silane-copolymerized polymers, corresponding monomers or prepolymers. Particularly preferred, therefore, are compositions comprising the carboxy-functionalized, silicon-containing precursor compound of the formula I, formula II or mixtures of these, having a solubility of more than 40% in a hydrocarbon-functionalized alkoxysilane or corresponding siloxane, more particularly in an alkenyl-functionalized alkoxysilane or siloxane, preferably in vinyltrimethoxysilane or vinyltriethoxysilane; more particularly the solubility is greater than 50% in hydrocarbon-functionalized alkoxysilane.

Compositions of the invention are especially suitable for use in a Monosil process, Sioplas process with thermoplastic base polymers, or in a copolymerization process with monomers and/or prepolymers of thermoplastic base polymers.

In particular the composition is substantially anhydrous, in order to prevent unwanted hydrolysis and/or condensation prior to the actual use in the Monosil, Sioplas process or co-condensation process.

The invention also provides compositions, more particularly for the crosslinking of thermoplastic base polymers, preferably as a formulation, comprising at least one silicon-containing precursor compound of different organic acids of the general formula I and/or II in line with the above definition, as component A, and optionally as component B a radical initiator and
optionally as component C an organofunctional silane compound,
more particularly an unsaturated alkoxysilane, preferably of the formula V,
$(B)_b SiR^4_c (OR^5)_{3-d-c}$ (V), where d, c, b, a, B, $R^4$ and $R^5$ are defined below, B being more preferably a vinyl group, and the unsaturated alkoxysilane being more particularly a vinyltriethoxysilane, vinyltrimethoxysilane or a mixture of these,
optionally the composition is in liquid form, for example as a silicon-containing precursor compound of the formula I and/or II, optionally together with a radical initiator, such as, preferably, dicumyl peroxide, tert-butyl cumyl peroxide, bis(tert-butylperoxy)di-isopropylbenzene, 1,1-di(tert-butylperoxy)-3,3,5-trimethylcyclohexane or 2,5-dimethyl-2,5-di-tert-butylperoxy-hexane, in an unsaturated alkoxysilane, such as vinyltrimethoxysilane or vinyltriethoxysilane; more particularly it is present in solution in the alkoxysilane,
optionally at least one of the above components A, B and/or C may be supported or encapsulated. Furthermore, the composition may also comprise formulating assistants and/or processing assistants as component(s) D, such as, for example, stabilizers or other customary formulating assistants.

Particularly preferred compositions, more particularly in the form of a formulation, comprise at least one silicon-containing precursor compound of different organic acids of the general formula I and/or II, or mixtures of these, in accordance with above definition as component A, with 1% to 25% by weight, more particularly 1.5% to 20% by weight, more preferably 2.0% to 18.0% by weight, and all values inbetween, optionally as component B a radical initiator with 1% to 12% by weight, more particularly 1.5% to 11% by weight, preferably 2% to 10% by weight, and more preferably 2.2% to 9.0% by weight, and also all values inbetween, and optionally, as component C, an organofunctional silane compound, more particularly an unsaturated alkoxysilane, preferably of the formula V, more preferably a vinyltrialkoxysilane, with 48% to 98% by weight, more particularly 55% to 97.5% by weight, preferably 60% to 95%, more preferably 70% to 92% by weight, very preferably 72% to 90% by weight, and also all values inbetween, and optionally as component(s) D with 0% to 15.0% by weight, more particularly 0.1% to 8.0% by weight, preferably 0.2% to 5.0% by weight, more preferably 0.5% to 3.0% by weight, and also all values inbetween, the aforementioned components independently of one another making a total in the composition of 100% by weight.

A preferred composition, preferably as a formulation which is suitable more particularly for the production of polymer compounds, comprises as component B at least one radical initiator. Preferred radical initiators are organic peroxides and/or organic peresters or mixtures of these, such as, preferably, tert-butyl peroxypivalate, tert-butyl peroxy-2-ethylhexanoate, dicumyl peroxide, di-tert-butyl peroxide, tert-butyl cumyl peroxide, 1,3-di(2-tert-butylperoxyisopropyl)benzene, 2,5-dimethyl-2,5-bis(tert-butylperoxy)hex-3-yne, di-tert-amyl peroxide, 1,3,5-tris(2-tert-butylperoxyisopropyl)benzene, 1-phenyl-1-tert-butylperoxyphthalide, alpha, alpha-bis(tert-butylperoxy)diisopropylbenzene, 2,5-dimethyl-2,5-di-tert-butylperoxyhexane, 1,1-di(tert-butylperoxy)-3,3,5-trimethylcyclohexane (TMCH). Useful may also be the use of n-butyl 4,4-di(tert-butylperoxy)valerate, ethyl 3,3-di(tert-butylperoxy)butylate and/or 3,3,6,9,9-hexamethyl-1,2,4,5-tetraoxacyclononane.

Likewise provided with the invention is a formulation comprising the composition of the invention or a compound of the formula I, II or mixtures of these.

Surprisingly it has been found that the composition which comprises a hydrolyzable precursor compound of at least two different organic acids of the general formulae I and/or II and optionally additionally an organofunctional silane compound, more particularly of the formula V, as defined below, can be reacted easily and economically with thermoplastic base polymers, monomers and/or prepolymers of the base polymers, to give polymer compounds, and does not have the identified disadvantages, such as toxicity and odor nuisance. Depending on composition, in addition, there are in all no alcohols released any more in the process for producing polymer compounds.

For example, if at least one silicon-containing precursor compound of different organic acids, for example of the general formula I with z=0, 1 or 2 and/or II, more particularly with z=0 or 1, and OR¹ corresponding to an unsaturated carboxylate radical, is grafted onto a base polymer or is copolymerized with a monomer and/or prepolymer of the base polymer, optionally in the presence of a radical initiator, or is mixed with a corresponding, carboxyl-substituted silane-grafted base polymer, and optionally, after shaping, a crosslinking takes place in the presence of moisture.

Additionally or alternatively the grafting or copolymerizing may take place in the presence of an organofunctional silane compound, such as an unsaturated alkoxysilane of the general formula V, as defined below.

With very particular preference the composition of the invention comprises as organofunctional silane compound, more particularly of the formula V, vinyltrimethoxysilane, vinyltriethoxysilane, vinylmethyldialkoxysilane, vinyltriethoxymethoxysilane (VTMOEO), vinyltriisopropoxysilane, vinyltri-n-butoxysilane, 3-methacryloyloxypropyltriethoxysilane, 3-methacryloyloxypropyltrimethoxysilane (MEMO) and/or vinylethoxydimethoxysilane and/or allylalkoxysilanes, such as allyltriethoxysilane, unsaturated siloxanes, such as preferably oligomeric vinylsiloxanes or mixtures of the stated compounds. Preferred organofunctional silane compounds contain either a vinyl or methacryloyl group, since these compounds are reactive toward radicals and are suitable for grafting to a polymer chain or for copolymerization with monomers, prepolymers.

The invention also provides a composition, more particularly having one or more of the aforementioned features, comprising a carboxy-functionalized, silicon-containing precursor compound which has at least two carboxyl groups functionalized with different hydrocarbon radicals, preferably three or four different carboxyl groups, and is obtained from the reaction of a halosilane of the general formula III,

where z is 0, 1 or 2 and x is 0, 1 or 2, with (x+z) less than or equal to 2, A as defined above and below, R² as defined, and Hal independently chlorine or bromine, with an at least molar stoichiometric ratio in relation to the halogen groups of the formula III with at least two different organic acids of the formula IV, i.e., of the formulae IVa and IVb as per subgroup, or preferably for z as 1 and x as 0, with an at least molar stoichiometric ratio in relation to the halogen groups of the formula III with at least two or three different organic acids of the formula IV, i.e., of the formulae IVa, IVb and/or IVc, or preferably for z as 0 and x as 0, with an at least molar stoichiometric ratio in relation to the halogen groups of the formula III with at least two, three or four different organic acids of the formula IV, i.e., formulae IVa, IVb, IVc and/or IVd, where in the different organic acids of the formula IV

R¹ (i.e., R$^{1a, 1b, 1c \text{ and/or } 1d}$) independently at each occurrence in formula IV corresponds to different carbonyl-R³ groups, in other words carbonyl-R$^{3a, 3b, 3c \text{ and/or } 3d}$, where R³ independently is selected from a substituted or unsubstituted hydrocarbon radical having 3 to 45 C atoms, more particularly having 7 to 45 C atoms, preferably 7 to 26 C atoms, more preferably 7 to 21 C atoms, or better 8 to 18 C atoms.

The different organic acids of the formula IV are preferably used approximately equimolarly, with the reaction taking place optionally in the presence of an inert solvent which is substantially removed after the reaction. The different acids of the formula IV may be used equimolarly to one another, in other words about 1:1 in the case of two different acids of the formula IV, or else in a ratio of 50:1 to 1:50 in each case for the different acids used, independently of whether two, three, four, five or six or even more different acids of the formula IV are used. The different acids are preferably used approximately equimolarly to one another, in other words, in the case of three different acids of the formula IV, about 1:1:1, and about 1:1:1:1 in the case of four different acids of the formula IV. Generally speaking, the skilled person knows that the molar ratios of the different organic acids to one another can be selected freely, the overall product being a carboxy-functionalized, silicon-containing precursor compound having at least two carboxyl groups, of the formula I or II, that are functionalized with different hydrocarbon radicals.

Where, preferably, a compound of the formula II is to be prepared, operation takes place at relatively high temperatures and with addition of traces of water, and the reaction times are extended.

The reaction takes place preferably in an inert solvent, more particularly an organic inert solvent in which the compounds of the formula III, IV, I and/or II are soluble; preferably only the reactants III and IV are soluble therein. Preferred solvents are hydrocarbons, halogenated hydrocarbons or ethers, preference being given to using aromatic hydrocarbons, such as toluene. Generally speaking, the skilled person also knows of other customary inert solvents, more particularly hydrocarbon-based solvents. Their suitability, moreover, is dependent on whether they can be removed from the products in a temperature range which does not lead to any substantial reaction with the starting materials or to any substantial decomposition of the products of the formula I or II.

The invention also provides a process, more particularly for preparing a carboxy-functionalized, silicon-containing precursor compound of the formula I and/or II, preferably for preparing a composition comprising at least one carboxy-functionalized, silicon-containing precursor compound of an organic acid with at least two, preferably with three or four, carboxyl groups functionalized with different hydrocarbon radicals, more particularly of the formula I and/or II, by reacting a halosilane of the formula III

where z is 0, 1 or 2, x is 0, 1 or 2, and (z+x) is less than or equal to (≤) 2,

A independently is an unsubstituted or substituted hydrocarbon group, more particularly an unsubstituted or substituted linear, branched and/or cyclic alkyl, alkenyl, cycloalkenyl-alkylene having 1 to 8 C atoms in the divalent alkylene group, alkylaryl, arylalkylene, aryl, such as phenyl; methacryloyloxyalkyl and/or acryloyloxyalkyl group, R² independently at each occurrence is an unsubstituted linear, branched or cyclic alkyl group having 1 to 24 C atoms, or aryl group, and Hal in each case independently is a halogen group selected from chlorine or bromine, with at least two different organic acids of the formula IV, i.e., different formulae IV encompassing IVa, IVb, IVc and/or IVd, where in the different organic acids of the formula IV

R¹ (R¹=R$^{1a, 1b, 1c \text{ and/or } 1d}$) independently at each occurrence corresponds to a carbonyl-R³ group (R³= R$^{3a, 3b, 3c \text{ and/or } 3d}$), where R³ independently is selected from a substituted or unsubstituted hydrocarbon radical having 3 to 45 C atoms, more particularly having 7 to 45 C atoms, preferably 7 to 26 C atoms, and the organic acids are optionally present at least in a molar stoichiometric ratio to the halogen groups of the formula III, optionally in the presence of an inert solvent.

With particular preference the aforementioned organic carboxylic acids, more particularly the naturally occurring or synthetic fatty acids, more particularly the saturated and/or unsaturated fatty acids, are used as organic acids of the formula IV in the process of the invention. More particularly this may be a selection from capric acid, caprylic acid, stearic acid, palmitic acid, oleic acid, lauric acid, myristic acid, and behenic acid.

With particular preference in the process of the invention the different organic acids of the formula IV are used with one another in a ratio from 10:1 to 1:10; preferably the different acids of the formula IV are used with one another approximately equimolarly, and more particularly the different acids of the formula IV are used at least approximately equimolarly in relation to the halogen groups of the formula I.

Corresponding to one preferred embodiment, it is preferred if a halosilane of the formula III where (v) z is 1 and x is 0, and A corresponds to an unsubstituted or substituted hydrocarbon group, more particularly an alkyl, alkenyl, cyclohexenyl-alkylene having 1 to 8 C atoms in the divalent alkylene group, alkyl/aryl, arylalkylene, aryl, such as phenyl; methacryloyloxyalkyl and/or acryloyloxyalkyl group, is reacted with two or three different organic acids of the formula IV at least in a molar stoichiometric ratio in relation to the halogen groups of the formula III, or where (vi) z is 0 and x is 0 is reacted with two, three or four different organic acids of the formula IV at least in a molar stoichiometric ratio in relation to the halogen groups of the formula III where in the different organic acids of the formula IV

$HOR^1$ (IV)

$R^1$ independently at each occurrence corresponds to a carbonyl-$R^3$ group, where $R^3$ independently is selected from a substituted or unsubstituted hydrocarbon radical having 3 to 45 C atoms, more particularly having 7 to 45 C atoms, preferably 7 to 26 C atoms, more preferably 8 to 18 C atoms, more particularly 8 to 16 C atoms.

Preferred examples of A groups are $H_3C(CH_2)_2$—, $(H_9C_4)$—, $(H_{17}C_8)$—, $(H_{33}C_{16})$—, $H_2C=CH_2$—, $ClCH_2(CH_2)_2$—, $C_6H_9$—$(CH_2)_2$—, more particularly 3-$C_6H_9$—$(CH_2)_2$—, 2-$C_6H_9$—$(CH_2)_2$—, 1-$C_6H_9$—$(CH_2)_2$—, $C_6H_8$—$(CH_2)_2$—, 1,3-$C_6H_8$—$(CH_2)_2$— or 2,4-$C_6H_8$—$(CH_2)_2$—, more particularly cyclohex-3-enyl-2-ethylene and also isomers, such as cyclohex-2-enyl-2-ethylene or cyclohex-1-enyl-2-ethylene, and mixtures of these, or else cyclohexadienyl-alkylene groups having 1 to 16 C atoms, more particularly a cyclohexadienyl-ethylene group.

With particular preference two, three or four or more of the aforementioned saturated fatty acids and/or unsaturated fatty acids of the general formula IV, more particularly comprising IVa ($R^{1a}OH$), IVb ($R^{1b}OH$), IVc ($R^{1c}OH$) and/or IVd ($R^{1d}OH$), are reacted with a halosilane of the formula III. It is preferred to react three or four different fatty acids of the formula IV, in each case at 1 mol, with 1 mol of trichlorosilane or 1 mol of tetrachlorosilane of the formula III, preferably in an inert solvent.

Preferred halosilanes are propyltrichlorosilane, cyclohex-3-enyl-2-ethylene-trichlorosilane, cyclohex-2-enyl-2-ethylene-trichlorosilane, cyclohex-1-enyl-2-ethylene-trichlorosilane, chloro-3-propyl-trichlorosilane, vinyltrichlorosilane, allyl-trichlorosilane, tetrachlorosilane, n-/iso-/tert-butyl-trichlorosilane, octyltrichlorosilane, n-/iso-hexadecyltrichlorosilane.

With further preference the process is conducted such that additionally or alternatively to the aforementioned features a compound of the general formula III (v) with z as 1 and A as alkyl-, such as $H_3C(CH_2)_2$—, n-/iso-$(H_{33}C_{16})$—, $(H_{17}C_8)$—, $(H_9C_4)$—, alkenyl-, such as $H_2C=CH_2$—, haloalkyl-, such as $ClCH_2(CH_2)_2$—, $C_6H_9$—$(CH_2)_2$—, more particularly 3-$C_6H_9$—$(CH_2)_2$—, 2-$C_6H_9$—$(CH_2)_2$—, 1-$C_6H_9$—$(CH_2)_2$—, $C_6H_8(CH_2)_2$—, 1,3-$C_6H_8$—$(CH_2)_2$— or 2,4-$C_6H_8$—$(CH_2)_2$—, with Hal as bromine or chlorine, preferably Hal=Cl, is reacted with at least two or three different organic acids of the formula IV, where $R^1$, encompassing $R^{1a\ to\ 1c\ and/or\ 1d}$, independently is selected from —$COC_7H_{15}$, —$COC_9H_{19}$, $C_{11}H_{23}$, —$COC_{13}H_{27}$, —$COC_{15}H_{31}$, —$COC_{17}H_{35}$, and —$COC_{21}H_{43}$, or (vi) where z is 0 is reacted with at least two, three or four different organic acids of the formula IV, where $R^1$, encompassing $R^{1a\ to\ 1c\ and/or\ 1d}$, independently is selected from —$COC_7H_{45}$, —$COC_9H_{19}$, —$COC_{11}H_{23}$, —$COC_{13}H_{27}$, —$COC_{15}H_{31}$, —$COC_{17}H_{35}$, and —$C_{21}H_{43}$.

The aforementioned reaction takes place preferably with an at least equimolar mixture of the different acids of the formula IV in relation to the halogen groups of the halosilane of the formula III that is used.

Generally speaking, the organic acids with relatively long hydrophobic hydrocarbon radicals, as specified above, beginning with valeric acid, preferably capric acid, lauric acid and/or myristic acid, are highly suitable for the preparation of silanol condensation catalysts and as silanol condensation catalyst. The less hydrophobic acids, such as propionic acid, acetic acid, formic acid, are classed only as useful for the reaction with thermoplastic hydrophobic polymers. Correspondingly, the odor-intensive fatty acids as well, such as butyric acid and caprylic acid, on account of the pungent odor, are only useful or less suitable to unsuitable for use in a composition, masterbatch or a process of the invention. This is so especially when the polymers or polymer compounds to be produced are to be used further for the manufacture of drinking-water pipes.

Organic acids are understood to be carboxylic acids which have no sulfate or sulfonic acid groups, and more particularly they are organic acids corresponding to $R^3$—COOH.

Further useful acids from which the precursor compounds of the formula I and/or II with $R^3$—COO— and $R^1O$—, respectively, may be prepared are described above, under glutaric acid etc.

The silicon-containing precursor compound of different organic acids may be applied to carrier materials or fillers, which are described in detail at the outset. In terms of process engineering, this may be accomplished by melting or dissolving in an inert solvent and addition of the carrier materials or fillers, or in accordance with methods known per se to the skilled person.

Additionally or alternatively to the aforementioned process features, therefore, the prepared composition of a silicon-containing precursor compound of an organic acid of the formula I and/or II may be applied to a carrier material, to a filler, encapsulated and/or incorporated.

The invention additionally provides for the use of a compound of the formula I and/or II, of a composition of a compound of the formulae I and/or II or of a mixture of these as, more particularly catalyst precursor compound, preferably as silane hydrolysis catalyst and/or as silanol condensation catalyst, in the preparation of a silicon-containing polymer, polymer compound, an unfilled crosslinked polymer and/or a filled crosslinked polymer, in a Monosil, Sioplas and/or copolymerization process, more particularly in a Monosil process or Sioplas process with thermoplastic base polymers or in a copolymerization process with monomers and/or prepolymers of thermoplastic base polymers in the presence of at least one radical initiator;

for the preparation of unfilled Si-crosslinked, and/or for the preparation of filled Si-crosslinked polymer compounds; and/or of correspondingly filled Si-crosslinked or unfilled Si-crosslinked polymers based on thermoplastic base polymers which comprise filled polymers, preferably, as fillers, mineral particles and/or fibers, such as glass fibers, silicas, aluminum hydroxide, magnesium hydroxide, and also other fillers familiar to the skilled person.

The invention further provides as well for the use of a compound of the formula I and/or II, of a composition of a compound of the formulae I and/or II or of a mixture of these, in the presence of a thermoplastic base polymer, a silane-grafted base polymer, a silane-copolymerized base polymer and/or in the presence of a monomer and/or prepolymer of this base polymer, and/or mixtures of these, or the use together with an organofunctional silane compound, more particularly of the formula V as defined below, or together with other silanol condensation catalysts, more particularly comprising dibutyltin dilaurate, dioctyltin dilaurate, dioctyltin di(2-ethylhexanoate), dioctyltin di(isooctyl mercaptoacetate), dibutyltin dicarboxylate, mono-butyltin tris(2-ethylhexanoate), dibutyltin dineodecanoate, laurylstannoxane, dibutyltin diketonoate, dioctyltin oxide, dibutyltin diacetate, dibutyltin maleate, dibutyltin dichloride, dibutyltin sulfide, dibutyltin oxide, organotin oxides, monobutyltin dihydroxychloride, monobutyltin oxides, dibutyltin bis(isooctyl maleate), or in the production of articles, more particularly moldings, preferably of cables or pipes.

In accordance with one particularly preferred embodiment use is made of a compound of the formula I and/or II, of a composition of a compound of the formulae I and/or II or of a mixture of these, together with an organofunctional silane compound, more particularly together with an alkoxysilane, functionalized with an unsaturated group, of the general formula V, $$(B)_b SiR^4{}_c(OR^5)_{3-d-c} \qquad (V)$$

where independently of one another d is 0, 1, 2 or 3 and c is 0, 1, 2 or 3, with the proviso that in formula V c+d is less than or equal to ($\leq$) 3, where B independently at each occurrence is a monovalent group in formula V, more particularly an unsaturated hydrocarbon group, preferably $(R^7)_2C=C(R^7)$-$E_q$-, in which radicals $R^7$ are identical or different and $R^7$ is a hydrogen atom or a methyl group or a phenyl group, the group E represents a group from the series —CH$_2$—, —(CH$_2$)$_2$—, —(CH$_2$)$_3$—, —O(O)C(CH$_2$)$_3$— or —C(O)O—(CH$_2$)$_3$—, q is 0 or 1, or isoprenyl, hexenyl, cyclohexenyl, terpenyl, squalanyl, squalenyl, polyterpenyl, betulaprenoxy, cis/trans-polyisoprenyl, or corresponds to a group $R^6$-D$_P$-[C(R$^6$)=C(R$^6$)—C(R$^6$)=C(R$^6$)]$_t$-D$_p$-, in which radicals $R^6$ are identical or different and $R^6$ is a hydrogen atom or an alkyl group having 1 to 3 C atoms, or an aryl group or an aralkyl group, preferably a methyl group or a phenyl group, groups D are identical or different and D represents a group from the series —CH$_2$—, —(CH$_2$)$_2$—, —(CH$_2$)$_3$—, —O(O)C(CH$_2$)$_3$— or —C(O)O—(CH$_2$)$_3$—, and p is 0 or 1 and t is 1 or 2, more preferably a vinyl group;

$R^5$ is independently at each occurrence methyl, ethyl, n-propyl and/or isopropyl, $R^4$ is independently at each occurrence a substituted or unsubstituted hydrocarbon group, more particularly an alkyl group having 1 to 16 C atoms, or an aryl group.

Likewise provided by the invention is a formulation comprising the composition of the invention, more particularly a masterbatch comprising a composition or a compound of the formula I or II, more particularly for the crosslinking of thermoplastic base polymers, of the at least one silicon-containing precursor compound of an organic acid of the formula I and/or of the formula II, and a thermoplastic base polymer, a silane-grafted base polymer, a silane-copolymerized base polymer, a monomer of these base polymers, a prepolymer of these base polymers and/or mixtures of these, and optionally comprises a radical initiator.

Considered thermoplastic base polymers in the sense of the invention are the following compounds: a silane-grafted base polymer, a silane-copolymerized base polymer and/or monomer and/or prepolymer of these base polymers, or else silane block coprepolymers and/or comprise mixtures of these. The thermoplastic base polymer is preferably a nonpolar polyolefin, such as polyethylene, polypropylene or a polyvinyl chloride, or a silane-grafted polyolefin and/or silane-copolymerized polyolefin, and/or a copolymer of one or more olefins and one or more comonomers which contain polar groups. The thermoplastic base polymer may also function partly or entirely as a carrier material, as for example in a masterbatch comprising as carrier material a thermoplastic base polymer or a polymer and the silicon-containing precursor compound of an organic acid of the formula I and/or II, and optionally an organofunctional silane compound, more particularly of the formula V.

Preferred thermoplastic base polymers of the invention are, in particular, acrylonitrile-butadiene-styrene (ABS), polyamides (PA), polymethyl methacrylate (PMMA), polycarbonate (PC), polyethylene (PE), polypropylene (PP), polystyrene (PS), polyvinyl chloride (PVC), and also the ethylene-unit-based polymers ethylene-vinyl acetate copolymers (EVA), EPDM or EPM and/or celluloid or silane-copolymerized polymers, and, as monomers and/or prepolymers, precursor compounds of these base polymers, such as ethylene, propylene. Further thermoplastic base polymers are specified below.

Examples of silane-copolymerized thermoplastic base polymers are also ethylene-silane copolymers, as for example ethylene-vinyltrimethoxysilane copolymer, ethylene-vinyltriethoxysilane copolymer, ethylene-dimethoxyethoxysilane copolymer, ethylene-gamma-trimethoxysilane copolymer, ethylene-gamma-(meth)acryloyloxypropyltriethoxysilane copolymer, ethylene-gamma-acryloyloxypropyltriethoxysilane copolymer, ethylene-gamma-(meth)acryloyloxypropyltrimethoxysilane copolymer, ethylene-gamma-acryloyloxypropyltrimethoxysilane copolymer and/or ethylene-triacetoxysilane copolymer.

As nonpolar thermoplastic base polymers it is possible to use thermoplastics such as, in particular, a pure PE type, as for example PE-LD, PE-LLD, PE-HD, m-PE. Base polymers which carry polar groups result, for example, in improved fire behavior, i.e., lower flammability and smoke-gas density, and increase the filler accommodation capacity. Polar groups are, for example, hydroxyl, nitrile, carbonyl, carboxyl, acyl, acyloxy, carboalkoxy groups or amino groups and also halogen atoms, more particularly chlorine atoms. Not polar are olefinic double bonds or C—C triple bonds. Suitable polymers besides polyvinyl chloride are copolymers of one or more olefins and one or more comonomers which contain polar groups, e.g., vinyl acetate, vinyl propionate, (meth)acrylic acid, methyl (meth)acrylate, ethyl (meth)acrylate, butyl (meth)acrylate, acrylonitrile. Within the copolymers the polar groups are found, for example, in amounts of 0.1 to 50 mol %, preferably of 5 to 30 mol %, based on the polyolefin units. Particularly suitable base polymers are ethylene-vinyl acetate copolymers (EVA). For example, one suitable commercial copolymer contains 19 mol % of vinyl acetate units and 81 mol % of ethylene units.

Particularly suitable base polymers are polyethylene, polypropylene, and also correspondingly silane-modified polymers. The silane-grafted polymers may be present filled with fillers or unfilled and may optionally be moisture-crosslinked after a shaping operation.

The composition of the invention or the masterbatch is suitable as an addition in a Monosil, Sioplas and/or copolymerization process or procedure. In a particularly suitable way, the silane hydrolysis catalyst and/or silanol condensation catalyst of the general formula I and/or II becomes effective only when moisture, additionally, is added. Accordingly, the ultimate crosslinking of the unfilled or filled polymer generally takes place, in accordance with a known manner, in a water bath, in a steam bath, or else by atmospheric moisture at ambient temperatures (referred to as "ambient curing").

As a further component, the masterbatch may comprise a stabilizer and/or other adjuvants and/or mixtures of these.

The invention also provides a silicon-containing precursor compound of the general formula I and/or II.

The examples which follow elucidate the compositions of the invention, the masterbatch, and the processes of the invention in more detail, without restricting the invention to these examples.

Methods of Determination:

Hydrolyzable chloride (chloride) was titrated potentiographically with silver nitrate (for example, Metrohm, type 682 silver rod as indicator electrode and Ag/AgCl reference electrode or other suitable reference electrode). Total chloride content after Wurtzschmitt digestion. For this purpose, the sample is digested with sodium peroxide in a Wurtzschmitt bomb. Following acidification with nitric acid, chloride is measured potentiographically with silver nitrate, as above.

General Preparation Methods:

A) Preparation of carboxysilanes functionalized with different hydrocarbon radicals and containing different carbonyl groups, such as haloalkyl-, alkyl-, alkenyltricarboxyl-silane, which below are also referred to as A-tricarboxysilane, or tetracarboxysilane.

GENERAL EXAMPLES a) A-Tricarboxysilanes (formula I with z=1) are prepared by reacting 1 mol of a A-trichlorosilane, or, generally, a A-trihalosilane, with 3 mol or an excess of two or three different organic monocarboxylic acid of the formula IV selected from $R^{1a}OH$, $R^{1b}OH$, and $R^{1c}OH$, directly, or by reacting them in an inert solvent, more particularly at elevated temperature. Preference is given to reacting 1 mol of A-trichlorosilane with a mixture of 1 mol of a first organic monocarboxylic acid ($R^{1a}OH$), 1 mol of a second organic monocarboxylic acid ($R^{1b}OH$), and 1 mol of a third organic monocarboxylic acid ($R^{1c}OH$). In the case of reaction with only two different monocarboxylic acids, these acids may be used in a ratio of 1:2 to 2:1, preferably 1:1, i.e., each at 1.5 mol. The reaction takes place preferably at elevated temperature, as for example up to the boiling temperature of the solvent or around the boiling temperature of the organic fatty acid and/or organic acid.

b) Tetracarboxysilanes are prepared by reacting 1 mol of tetrahalosilane, more particularly tetrachlorosilane or tetrabromosilane, with 4 mol or an excess of two, more particularly three or four different monocarboxylic acids of the formula IV selected from $R^{1a}OH$, $R^{1b}OH$, $R^{1c}OH$, and $R^{1d}OH$, as for example different fatty acids or a fatty-acid mixture of these fatty acids. The reaction may take place directly by melting or in an inert solvent, preferably at elevated temperature.

Procedure

Preparation, characterization of following carboxysilanes from TSC, VTC and STC with 3 (or 4) different, long-chain carboxylic acids in terms of aggregate state (solid, wax, liquid)

Example 1

Preparation of Vinylcarboxysilanes

Example 1.1

Vinylcarboxysilane from Lauric, Myristic, and Caprylic Acid

TABLE 1

Overview

| | | A-/$R^{3a-c}$ | | A-/$R^{1a-c}$ | |
|---|---|---|---|---|---|
| Vinyltrichlorosilane (VTC) | A | $H_2C$=CH | A | $H_2C$=CH | |
| Caprylic acid | $R3^a$ | $C_7H_{15}$ | $R^{1a}$ | —(CO)$C_7H_{15}$ | |
| Lauric acid | $R3^b$ | $C_{11}H_{23}$ | $R^{1b}$ | —(CO)$C_{11}H_{23}$ | |
| Myristic acid | $R3^c$ | $C_{13}H_{27}$ | $R^{1c}$ | —(CO)$C_{13}H_{27}$ | |

Procedure: Synthesis with three different fatty acids (=<C14) with vinyltrichlorosilane (VTC); experimental batch: 200 g (Chain length $R^1$ of the fatty acids $R^{1a-c}$=C8, C12, C14)

TABLE 2

Reactants

| Reactants | m(actual) [g] | Amount of substance [mol] | Molar mass [g/mol] |
|---|---|---|---|
| Vinyltrichlorosilane | 44.0 | 1 | 161.49 |
| Lauric acid | 54.4 | 1 | 200.3 |
| Myristic acid | 62.2 | 1 | 228.4 |
| Caprylic acid (liquid) | 39.3 | 1 | 144.2 |
| Toluene | 101.2 | | 92.14 |

TABLE 3

| | Product (target) | | | |
|---|---|---|---|---|
| Product | Molar mass | mol | Mass (%) | Mass (target) |
| Carboxysilane | 624.5 | 1 | 85.1% | 170.2 |
| HCl | 36.5 | 3 | 14.9% | 29.8 |

Synthesis

The stated fatty acids were introduced with 100 g of toluene into the reaction flask and were mixed and heated to around 60° C. Using a dropping funnel, vinyltrichlorosilane was added dropwise over the course of 15 minutes. A slight rise in temperature can be observed. Following the addition, stirring is carried out for 15 minutes, after which the temperature of the oil bath is increased to 150° C. In the course of the subsequent stirring, evolution of gas (HCl gas) was observable. A wash bottle filled with NaOH+water was used to neutralize HCl. Stirring was continued for 3.5 hours.

Distillation

The oil bath was heated to 80° C. Vapors were taken off into a cold trap (dry ice and isopropanol, about −80° C.) on a rotary evaporator at a pressure of <1 mbar. This is followed by stirring for 1 hour.

The product obtained is liquid, slightly viscous, and slightly yellow. Toluene was removed predominantly on the rotary evaporator.

Final mass: Carboxysilane: 169.9 g (yield 99.82%)

NMR Analysis of the Carboxysilane

The 1H and 13C NMR spectra show the reaction product of vinyltrichlorosilane with the different fatty acids. Fractions of excess free acid are present (about 8 mol %).

$^{29}$Si NMR Spectrum about 4.7% Si in the silane region about 84.0% Si in the vinyltricarboxysilane region about 11.3% Si M structures derived from vinyltricarboxysilane Chloride determination: Additionally, a chloride determination was carried out on the carboxysilane prepared.

TABLE 4

| | Chloride determination | |
|---|---|---|
| Determination | Result | Unit |
| Chloride | 0.39 | % (mass) |
| Total chloride | 0.46 | % (mass) |

Solubility Investigation in Solvent:

TABLE 5

| Solubility | |
|---|---|
| Solubility | in vinyltrimethoxysilane |
| Carboxysilane | >50% |

A liquid, slightly yellow, and slightly viscous vinylcarboxysilane of the three different fatty acids was prepared.

Example 1.2

Vinylcarboxysilane from Myristic, Palmitic and Stearic Acid

TABLE 6

| | Overview | | | |
|---|---|---|---|---|
| | A-/$R^{3a-c}$- | | A-/$R^{1a-c}$- | |
| Vinyltrichlorosilane (VTC) | A | $H_2C=CH$ | A | $H_2C=CH$ |
| Myristic acid | $R^{3a}$ | $C_{13}H_{27}$ | $R^{1a}$ | —(CO)$C_{13}H_{27}$ |
| Palmitic acid | $R^{3b}$ | $C_{15}H_{31}$ | $R^{1b}$ | —(CO)$C_{15}H_{31}$ |
| Stearic acid | $R^{3c}$ | $C_{17}H_{35}$ | $R^{1c}$ | —(CO)$C_{17}H_{35}$ |

Procedure: Preparation of vinyltricarboxysilane with a mixture of three different fatty acids (>=C14) with vinyltrichlorosilane (VTC); experimental batch: 200 g (Chain length $R^1$ of the fatty acids $R^{1a-c}$=C14, C16, C18)

TABLE 7

| | Reactants I | | |
|---|---|---|---|
| Reactants | m(actual) [g] | Amount of substance [mol] | Molar mass [g/mol] |
| VTC | 34.7 | 1 | 161.49 |
| Stearic acid | 61.1 | 1 | 284.5 |
| Myristic acid | 49.1 | 1 | 228.4 |
| Palmitic acid | 55.1 | 1 | 256.4 |
| Toluene | 101.0 | | 92.14 |

TABLE 8

| | Product (target) | | | |
|---|---|---|---|---|
| Product | Molar mass | mol | Mass (%) | Mass (target) |
| Carboxysilane | 820.9 | 1 | 88.2% | 176.5 |
| HCl | 36.5 | 3 | 11.8% | 23.5 |

Synthesis

The three fatty acids were introduced with 100 g of toluene into the reaction flask and were mixed and heated to around 60° C. Using a dropping funnel, vinyltrichlorosilane was added dropwise over the course of 15 minutes. A slight rise in temperature was observable. Following the addition, stirring is carried out for 15 minutes, after which the temperature of the oil bath is increased to 150° C. In the course of the subsequent stirring, evolution of gas (HCl gas) was observable. A wash bottle filled with NaOH+ water was used to neutralize HCl. Stirring was continued for 3.5 hours.

Distillation

Volatile constituents were taken off at an oil bath temperature of 85° C. on a rotary evaporator (pressure at <1 mbar; cold trap, with dry ice and isopropanol to about −80° C.). This was followed by stirring for 1 hour. The product was a white solid. 97.5% of the toluene was captured in the cold trap.

Final mass: Carboxysilane: 174.3 g (yield 99.75%)

NMR Analysis of the Carboxysilane

The $^1$Hl and $^{13}$C NMR spectra show the reaction product of vinyltrichlorosilane with the fatty acids. Fractions of excess free acid are present (about 10 mol %).

$^{29}$Si NMR Spectrum about 2% Si in the silane region about 82.1% Si in the vinyltricarboxysilane region about 15.8% Si M structures derived from vinyltricarboxysilane Chloride determination: Additionally, a chloride determination was carried out on the carboxysilane prepared.

TABLE 9

| Chloride determination | | |
|---|---|---|
| Determination | Result | Unit |
| Total chloride | <0.1 | % (mass) |

Solubility Investigation in Solvent:

TABLE 10

| Solubility | |
|---|---|
| Solubility | vinyltrimethoxysilane (VTMO) |
| Carboxysilane | <1.0% |

A solid, white vinylcarboxysilane was prepared with the three different fatty acids.

Example 2

Preparation of Vinylcarboxysilanes with Propyltrichlorosilane (PTCS)

Example 2.1

Preparation of Propyltricarboxysilane

TABLE 11

| Overview | | | | |
|---|---|---|---|---|
| | | A-/R$^{3a-c}$- | | A-/R$^{1a-c}$- |
| Vinyltrichlorosilane (VTC) | A | C$_3$H$_7$ | A | —(CO)C$_3$H$_7$ |
| Caprylic acid | R$^{3a}$ | C$_7$H$_{15}$ | R$^{1a}$ | —(CO)C$_7$H$_{15}$ |
| Lauric acid | R$^{3b}$ | C$_{11}$H$_{23}$ | R$^{1b}$ | —(CO)C$_{11}$H$_{23}$ |
| Myristic acid | R$^{3c}$ | C$_{13}$H$_{27}$ | R$^{1c}$ | —(CO)C$_{13}$H$_{27}$ |

Procedure: Synthesis with three different fatty acids (=<C14) with propyltrichlorosilane (PTCS); experimental batch: 200 g (Chain length of the different fatty acids R$^{1a-c}$=C8, C12, C14)

TABLE 12

| Reactants | | | |
|---|---|---|---|
| Reactants | m(actual) [g] | Amount of substance [mol] | Molar mass [g/mol] |
| Propyltrichlorosilane (PTCS) | 47.3 | 1 | 177.5 |
| Lauric acid | 53.4 | 1 | 200.3 |
| Myristic acid | 60.9 | 1 | 228.4 |
| Caprylic acid (liquid) | 38.4 | 1 | 144.2 |
| Toluene | 100.0 | | 92.14 |

TABLE 13

| Product (target) | | | | |
|---|---|---|---|---|
| Product | Molar mass | mol | Mass (%) | Mass (target) |
| Propylcarboxysilane | 641.0 | 1 | 85.4% | 170.8 |
| HCl | 36.5 | 3 | 14.6% | 29.2 |

Synthesis

The three fatty acids were introduced with 100 g of toluene into the reaction flask and were mixed and heated to around 60° C. Using a dropping funnel, propyltrichlorosilane (PTCS) was added dropwise over the course of 15 minutes. No rise in temperature was observable. Following the addition, stirring was carried out for 15 minutes, after which the temperature of the oil bath was increased to 150° C. In the course of the subsequent stirring, evolution of gas (HCl gas) was observable. A wash bottle filled with NaOH+water was used to neutralize the HCl. Stirring was continued for 3.5 hours.

Distillation

The oil bath of a rotary evaporator was heated to 85° C. (pressure at <1 mbar; cold trap, with dry ice and isopropanol to about −80° C.) and volatile constituents were taken off. This was followed by stirring for 1 hour. 98.2% of the toluene was removed by distillation. This gave a liquid, slightly viscous, slightly yellow product.

Final mass: Carboxysilane: 167.7 g (98.13%)

NMR Analysis of the Carboxysilane

The $^1$H and $^{13}$C NMR spectra show the reaction product of propyltrichlorosilane with the fatty acids. Additionally there is about 5% of free acid present.

$^{29}$Si NMR Spectrum about 90.0% Si in the tricarboxysilane region about 8.1% Si M structures about 1.9% Si additional signal at −24 ppm (silicone)

Chloride determination: Additionally, a chloride determination was carried out on the carboxysilane prepared.

TABLE 14

| Chloride determination | | |
|---|---|---|
| Determination | Result | Unit |
| Total chloride | <0.15 | % (Mass) |

Solubility Investigation in Different Solvents:

TABLE 15

| Solubility | |
|---|---|
| Solubility | Vinyltrimethoxysilane (VTMO) |
| Carboxysilane | >50% |

A liquid, slightly yellow, slightly viscous propylcarboxysilane of the three different fatty acids was prepared.

Example 2.2

Propyltrichlorosilane with Myristic, Palmitic and Stearic Acid

TABLE 16

Overview

| | | A-/R$^{3a-c}$- | | A-/R$^{1a-c}$- |
|---|---|---|---|---|
| Propyltrichlorosilane (PTCS) | A | $C_3H_7$ | A | —(CO)$C_3H_7$ |
| Myristic acid | $R^{3a}$ | $C_{13}H_{27}$ | $R^{1a}$ | —(CO)$C_{13}H_{27}$ |
| Palmitic acid | $R^{3b}$ | $C_{15}H_{31}$ | $R^{1b}$ | —(CO)$C_{15}H_{31}$ |
| Stearic acid | $R^{3c}$ | $C_{17}H_{35}$ | $R^{1c}$ | —(CO)$C_{17}H_{35}$ |

Procedure: Synthesis with different fatty acids (>=C14) with propyltrichlorosilane (PTCS); experimental batch: 200 g (Chain length of the fatty acids $R^{1a-c}$—: C14, C16, C18)

TABLE 17

| Reactants | m(actual) [g] | Amount of substance [mol] | Molar mass [g/mol] |
|---|---|---|---|
| Propyltrichlorosilane (PTCS) | 37.5 | 1 | 177.5 |
| Stearic acid | 60.1 | 1 | 284.5 |
| Myristic acid | 48.2 | 1 | 228.4 |
| Palmitic acid | 54.2 | 1 | 256.4 |
| Toluene | 100.0 | | 92.14 |

TABLE 18

Product (target)

| Product | Molar mass | mol | Mass (%) | Mass (target) |
|---|---|---|---|---|
| Propylcarboxysilane | 837.4 | 1 | 88.4% | 176.9 |
| HCl | 36.5 | 3 | 11.6% | 23.1 |

Synthesis

The three fatty acids were introduced with 100 g of toluene into the reaction flask and were mixed and heated to around 60° C. Using a dropping funnel, propyltrichlorosilane (PTCS) was added dropwise over the course of 15 minutes. No rise in temperature could be observed. Following the addition, stirring was carried out for 15 minutes, after which the temperature of the oil bath was increased to 150° C. In the course of the subsequent stirring, evolution of gas (HCl gas) was observable. A wash bottle filled with NaOH+water was used, with a slight underpressure, to neutralize HCl. Stirring was continued for 3.5 hours.

Distillation

The oil bath of a rotary evaporator was heated to 85° C. (pressure to <1 mbar; cold trap, with dry ice and isopropanol to about −80° C.) and the volatile constituents were taken off. This was followed by stirring for 1 hour. The toluene was removed substantially by distillation. This gave a white, solid product.

Final mass: Carboxysilane: 174.0 g (98.3%)

NMR Analysis of the Carboxysilane

The $^1$H and $^{13}$C NMR spectra show the reaction product of propyltrichlorosilane with the three fatty acids. Additionally there is about 13% of free acid present.

$^{29}$Si NMR Spectrum about 74.6% Si in the carboxysilane region
about 22.3% Si M structures (derived from the carboxysilanes)
about 0.4% Si D structures (derived from the carboxysilanes)
about 2.7% Si additional signal at −24 ppm (silicone)

Chloride determination: Additionally, a chloride determination was carried out on the carboxysilane prepared.

TABLE 19

Chloride determination

| Determination | Result | Unit |
|---|---|---|
| Total chloride | <0.1 | % (Mass) |

Solubility Investigation in the Solvent

TABLE 20

Solubility

| Solubility | Vinyltrimethoxysilane (VTMO) |
|---|---|
| Carboxysilane | <1% |

A solid, white propylcarboxysilane was prepared of the three different fatty acids.

Example 3

Reaction of Tetrachlorosilane (SiCl$_4$) with Different Fatty Acids

Example 3.1

Tetrachlorosilane with Caprylic, Capric, Lauric and Myristic Acid

TABLE 21

Overview

| | | $R^{3a-cd}$ | | $R^{1a-cd}$ |
|---|---|---|---|---|
| Caprylic acid | $R^{3a}$ | $C_7H_{15}$ | $R^{1a}$ | —(CO)$C_7H_{15}$ |
| Capric acid | $R^{3b}$ | $C_9H_{19}$ | $R^{1b}$ | —(CO)$C_9H_{19}$ |
| Lauric acid | $R^{3c}$ | $C_{11}H_{23}$ | $R^{1c}$ | —(CO)$C_{11}H_{23}$ |
| Myristic acid | $R^{3d}$ | $C_{13}H_{27}$ | $R^{1d}$ | —(CO)$C_{13}H_{27}$ |

Procedure: Synthesis with four different fatty acids (=<C14) and tetrachlorosilane (SiCl$_4$), experimental batch: 200 g (Chain length of the fatty acids $R^{1a-cd}$: C8, C10, C12, C14)

TABLE 22

Reactants

| Reactants | m(actual) [g] | Amount of substance [mol] | Molar mass [g/mol] |
|---|---|---|---|
| Tetrachlorosilane/ SiCl$_4$ | 37.1 | 1 | 169.9 |
| Lauric acid | 43.8 | 1 | 200.3 |
| Myristic acid | 49.9 | 1 | 228.4 |
| Caprylic acid (liquid) | 31.5 | 1 | 144.2 |
| Capric acid | 37.7 | 1 | 172.3 |
| Toluene | 100.0 | | 92.14 |

TABLE 23

| Product | Molar mass | mol | Mass (%) | Mass (target) |
|---|---|---|---|---|
| Silicon carboxysilane | 769.3 | 1 | 84.0% | 168.1 |
| HCl | 36.5 | 4 | 16.0% | 31.9 |

Synthesis

The four fatty acids were introduced into the reaction flask with 100 g of toluene, mixed and heated to about 50° C. By means of a dropping funnel, tetrachlorosilane ($SiCl_4$) was added dropwise over the course of 15 minutes. No increase in temperature could be observed. Following the addition, stirring was continued for 15 minutes, after which the temperature of the oil bath was raised to 150° C. During the subsequent stirring, the evolution of gas (HCl gas) was observable. A wash bottle filled with NaOH+water was used, with a slight underpressure, to neutralize HCl. Stirring was continued for 3.5 hours.

Distillation

The oil bath of the rotary evaporator was heated to 85° C. (pressure to <1 mbar, cold trap, with dry ice and isopropanol to about −80° C.) and volatile constituents were taken off. This was followed by stirring for 1 hour. Toluene was removed substantially completely by distillation. The product is liquid, slightly viscous, and slightly yellow.

Final mass: Carboxysilane: 164.4 g (97.800)

NMR Analysis of the Carboxysilane

The $^1H$ and $^{13}C$ NMR spectra show the reaction product of tetrachlorosilane with the four fatty acids. Additionally there is about 150 of free acid present.

$^{29}Si$ NMR Spectrum about 60.0% Si in the tetracarboxysilane region about 35.5% Si M structures derived from the tetracarboxysilane about 4.5% Si D structures derived from the tetracarboxysilane Chloride determination: Additionally, a chloride determination was carried out on the carboxysilane prepared.

TABLE 24

| Determination | Result | Unit |
|---|---|---|
| Total chloride | 400 (<0.1) | mg/kg (% mass) |

Chloride determination

Solubility Investigation in Solvent

TABLE 25

Solubility

| Solubility | Vinyltrimethoxysilane (VTMO) |
|---|---|
| Carboxysilane | >50% |

A liquid, slightly yellow, slightly viscous silicon carboxysilane of the four different fatty acids was prepared.

Example 3.2

Tetrachlorosilane with Myristic, Palmitic, Stearic and Behenic Acid

TABLE 26

Overview

| | | $R^{3a\text{-}cd}\text{-}$ | | $R^{1a\text{-}cd}\text{-}$ |
|---|---|---|---|---|
| Myristic acid | $R^{3a}$ | $C_{13}H_{27}$ | $R^{1a}$ | —(CO)$C_{13}H_{27}$ |
| Palmitic acid | $R^{3b}$ | $C_{15}H_{31}$ | $R^{1b}$ | —(CO)$C_{15}H_{31}$ |
| Stearic acid | $R^{3c}$ | $C_{17}H_{35}$ | $R^{1c}$ | —(CO)$C_{17}H_{35}$ |
| Behenic acid | $R^{3d}$ | $C_{21}H_{43}$ | $R^{1d}$ | —(CO)$C_{21}H_{43}$ |

Procedure

Synthesis with four different fatty acids (>=C14) with tetrachlorosilane ($SiCl_4$), Experimental batch: 200 g (Chain length of the fatty acids $R^{1a\text{-}cd}$—: C14, C16, C18, C22)

TABLE 27

Reactants

| Reactants | m(actual) [g] | Amount of substance [mol] | Molar mass [g/mol] |
|---|---|---|---|
| Tetrachlorosilane ($SiCl_4$) | 26.6 | 1 | 169.9 |
| Stearic acid | 44.5 | 1 | 284.5 |
| Myristic acid | 35.7 | 1 | 228.4 |
| Palmitic acid | 40.1 | 1 | 256.4 |
| Behenic acid | 53.2 | 1 | 340.6 |
| Toluene | 100.0 | | 92.14 |

TABLE 28

Product (target)

| Product | Molar mass | mol | Mass (%) | Mass (target) |
|---|---|---|---|---|
| Silicon carboxysilane | 1135.0 | 1 | 88.6% | 177.2 |
| HCl | 36.5 | 4 | 11.4% | 22.8 |

Synthesis

The four fatty acids were introduced with 100 g of toluene into the reaction flask, mixed and heated to about 50° C. Using a dropping funnel, tetrachlorosilane ($SiCl_4$) was added dropwise over the course of 15 minutes. No temperature rise could be observed. Following the addition, stirring was continued for 15 minutes, after which the temperature of the oil bath was raised to 150° C. During the subsequent stirring, the evolution of gas (HCl gas) was observable. A wash bottle filled with NaOH+water was used, with a slight underpressure, to neutralize HCl. Stirring was continued for 3.5 hours.

Distillation

The oil bath of the rotary evaporator was heated to 85° C. (pressure to <1 mbar, cold trap, with dry ice and isopropanol to about −80° C.) and volatile constituents were taken off. This was followed by stirring for 1 hour. Toluene was removed substantially completely. This gave a white, solid product.

Final mass: Carboxysilane: 174.1 g (97.80%)

NMR Analysis of the Carboxysilane

The $^1H$ and $^{13}C$ NMR spectra of the sample show tetracarboxysilane with the different fatty acid residues and additional fractions of free carboxylic acid (about 15%).

$^{29}$Si NMR Spectrum 66.3% Si tetracarboxysilane 28.3% Si M structures derived from tetracarboxysilane 5.4% Si D structures derived from tetracarboxysilane Chloride determination: Additionally, a chloride determination was carried out on the carboxysilane prepared.

TABLE 29

| Chloride determination | | |
|---|---|---|
| Determination | Result | Unit |
| Total chloride | <0.1 | % (mass) |

Solubility Investigation in Solvent

TABLE 30

| Solubility | |
|---|---|
| Solubility | Vinyltrimethoxysilane (VTMO) |
| Carboxysilane | <1% |

A solid, white silicon carboxysilane of the four different fatty acids was prepared.

Example 3.3

Tetrachlorosilane with Caprylic, Palmitic, Stearic and Behenic Acid

TABLE 31

| Overview | | | | |
|---|---|---|---|---|
| | $R^{3a\text{-}cd}$- | | $R^{1a\text{-}cd}$- | |
| Caprylic acid | $R^{3a}$ | $C_7H_{15}$ | $R^{1a}$ | —(CO)$C_7H_{15}$ |
| Palmitic acid | $R^{3b}$ | $C_{15}H_{31}$ | $R^{1b}$ | —(CO)$C_{15}H_{31}$ |
| Stearic acid | $R^{3c}$ | $C_{17}H_{35}$ | $R^{1c}$ | —(CO)$C_{17}H_{35}$ |
| Behenic acid | $R^{3d}$ | $C_{21}H_{43}$ | $R^{1d}$ | —(CO)$C_{21}H_{43}$ |

Procedure

Synthesis with four different fatty acids with tetrachlorosilane (SiCl$_4$),

Experimental batch: 200 g (Chain length of the fatty acids $R^{1a\text{-}cd}$—: C8, C16, C18, C22)

TABLE 32

| Reactants | | | |
|---|---|---|---|
| Reactants | m(actual) [g] | Amount of substance [mol] | Molar mass [g/mol] |
| Tetrachlorosilane SiCl$_4$ | 28.4 | 1 | 169.9 |
| Stearic acid | 47.6 | 1 | 284.5 |
| Caprylic acid (liquid) | 24.1 | 1 | 144.2 |
| Palmitic acid | 42.9 | 1 | 256.4 |
| Behenic acid | 57.0 | 1 | 340.6 |
| Toluene | 100.0 | | 92.14 |

TABLE 33

| | Product (target) | | | |
|---|---|---|---|---|
| Product | Molar mass | mol | Mass (%) | Mass (target) |
| Silicon carboxysilane | 1149.7 | 1 | 87.8% | 175.6 |
| HCl | 36.5 | 4 | 12.2% | 24.4 |

Synthesis

The four fatty acids were introduced with 100 g of toluene into the reaction flask, mixed and heated to about 50° C. Using a dropping funnel, tetrachlorosilane (SiCl$_4$) was added dropwise over the course of 15 minutes. No temperature rise could be observed. Following the addition, stirring was continued for 15 minutes, after which the temperature of the oil bath was raised to 150° C. In the course of the subsequent stirring, the evolution of gas (HCl gas) was observable. A wash bottle filled with NaOH+water was used, with a slight underpressure, to neutralize HCl. Stirring was continued for 3.5 hours.

Distillation

The oil bath of the rotary evaporator was heated to 85° C. (pressure to <1 mbar, cold trap, with dry ice and isopropanol to about −80° C.) and volatile constituents were taken off. This was followed by stirring for 1 hour. The toluene was removed substantially completely. This gave a solid, white product.

Final Mass: Carboxysilane: 172.2 g (98.06%)

NMR Analysis of the Carboxysilane

The $^1$H and $^{13}$C NMR spectra of the sample show tetracarboxysilane of the different fatty acids with additional fractions of free carboxylic acid (about 20%).

$^{29}$Si NMR Spectrum 60.5% Si tetracarboxysilane 28.5% Si M structures derived from tetracarboxysilane 11.0% Si D structures derived from tetracarboxysilane Chloride determination: Additionally, a chloride determination was carried out on the carboxysilane prepared.

TABLE 34

| Chloride determination | | |
|---|---|---|
| Determination | Result | Unit |
| Total chloride | <0.1 | % (mass) |

Solubility Investigation in Solvent

TABLE 35

| Solubility | |
|---|---|
| Solubility | Vinyltrimethoxysilane (VTMO) |
| Carboxysilane | <1% |

A carboxysilane was synthesized from SiCl$_4$ with three long-chain fatty acids and one short-chain fatty acid. The short-chain fatty acid, however, had no effect on the consistency of the silicon carboxysilane. A solid, white product was obtained.

Example 4

Reaction of 3-Chloropropyltrichlorosilane (CPTCS) with Different Fatty Acids

The CPTCS was purified via a Vigreux column.

Example 4.1

Reaction CPTCS with Caprylic, Capric, Lauric and Myristic Acid

TABLE 36

Overview

|  |  | $R^{3a\text{-}cd}$- |  | $R^{1a\text{-}cd}$- |
|---|---|---|---|---|
| Caprylic acid | $R^{3a}$ | $C_7H_{15}$ | $R^{3a}$ | —(CO)$C_7H_{15}$ |
| Capric acid | $R^{3b}$ | $C_9H_{19}$ | $R^{1b}$ | —(CO)$C_9H_{19}$ |
| Lauric acid | $R^{3c}$ | $C_{11}H_{23}$ | $R^{1c}$ | —(CO)$C_{11}H_{23}$ |
| Myristic acid | $R^{3d}$ | $C_{13}H_{27}$ | $R^{1d}$ | —(CO)$C_{13}H_{27}$ |

Synthesis with four different fatty acids with 3-chloropropyltrichlorosilane (CPTCS)
Experimental batch: 200 g
(Chain length of the fatty acids $R^{1a\text{-}cd}$—: C8, C10, C12, C14)

TABLE 37

Reactants

| Reactants | m(actual) [g] | Amount of substance [mol] | Molar mass [g/mol] |
|---|---|---|---|
| CPTCS | 44.3 | 1 | 212.0 |
| Lauric acid | 41.9 | 1 | 200.3 |
| Myristic acid | 47.7 | 1 | 228.4 |
| Caprylic acid (liquid) | 30.1 | 1 | 144.2 |
| Capric acid | 36.0 | 1 | 172.3 |
| Toluene | 100.0 |  | 92.14 |

TABLE 38

Product (target)

| Product | Molar mass | mol | Mass (%) | Mass (target) |
|---|---|---|---|---|
| Propylcarboxysilane | 811.2 | 1 | 84.7% | 169.5 |
| HCl | 36.5 | 4 | 12.2% | 30.5 |

Synthesis
The four fatty acids were introduced with 100 g of toluene into the reaction flask, mixed and heated to about 50° C. Using a dropping funnel, chloropropyltrichlorosilane (CPTCS) was added dropwise over the course of 15 minutes. No temperature rise could be observed. Following the addition, stirring was continued for 15 minutes, after which the temperature of the oil bath was raised to 150° C. In the course of the subsequent stirring, the evolution of gas (HCl gas) was observable. A wash bottle filled with NaOH+water was used, with a slight underpressure, to neutralize HCl. Stirring was continued for 3.5 hours.

Distillation
The oil bath of the rotary evaporator was heated to 85° C. (pressure to <1 mbar, cold trap, with dry ice and isopropanol to about −80° C.) and volatile constituents were taken off. This was followed by stirring for 1 hour. Toluene was removed substantially completely. This gave a liquid, slightly viscous, and slightly yellow product.
Final mass: Carboxysilane: 173.8 g
NMR Analysis of the Carboxysilane
The $^1$H and $^{13}$C NMR spectra show the reaction product of chloro-propyltrichlorosilane with the different fatty acids. The chlorine atoms on the silicon were replaced, while the chloropropyl radical remains unchanged. Correspondingly, there are fractions of excess free acid present.
$^{29}$Si NMR Spectrum
about 82.8% Si in the silane region (chloropropyltricarboxysilane)
about 17.2% Si M structures
Chloride determination: Additionally, a chloride determination was carried out on the carboxysilane prepared.

TABLE 39

Chloride determination

| Determination | Result | Unit |
|---|---|---|
| Total chloride | 4.35 | % (mass) |

Solubility Investigation in Solvent

TABLE 40

Solubility

| Solubility | Vinyltrimethoxysilane (VTMO) |
|---|---|
| Carboxysilane | >50% |

A liquid, slightly viscous propylcarboxysilane of the three different fatty acids was prepared.

Example 4.2

CPTCS with Myristic, Palmitic, Stearic and Behenic Acid

TABLE 41

Overview

|  |  | $R^{3a\text{-}cd}$- |  | $R^{1a\text{-}cd}$- |
|---|---|---|---|---|
| Myristic acid | $R^{3a}$ | $C_{13}H_{27}$ | $R^{1a}$ | —(CO)$C_{13}H_{27}$ |
| Palmitic acid | $R^{3b}$ | $C_{15}H_{31}$ | $R^{1b}$ | —(CO)$C_{15}H_{31}$ |
| Stearic acid | $R^{3c}$ | $C_{17}H_{35}$ | $R^{1c}$ | —(CO)$C_{17}H_{35}$ |
| Behenic acid | $R^{3d}$ | $C_{21}H_{43}$ | $R^{1d}$ | —(CO)$C_{21}H_{43}$ |

Synthesis with four different fatty acids with 3-chloropropyltrichlorosilane (CPTCS),
Experimental batch: 200 g
(Chain length of the fatty acids $R^{1a\text{-}cd}$—: C14, C16, C18, C22)

TABLE 42

Reactants

| Reactants | m(actual) [g] | Amount of substance [mol] | Molar mass [g/mol] |
|---|---|---|---|
| CPTCS | 26.6 | 1 | 212.0 |
| Stearic acid | 43.0 | 1 | 284.5 |
| Myristic acid | 34.6 | 1 | 228.4 |
| Palmitic acid | 38.8 | 1 | 256.4 |
| Behenic acid | 51.5 | 1 | 340.6 |
| Toluene | 100.0 | | 92.14 |

TABLE 43

Product (target)

| Product | Molar mass | mol | Mass (%) | Mass (target) |
|---|---|---|---|---|
| Propylcarboxysilane | 1176.1 | 1 | 89.0% | 177.9 |
| HCl | 36.5 | 4 | 11.0% | 22.1 |

Synthesis

The four fatty acids were introduced with 100 g of toluene into the reaction flask, mixed and heated to about 50° C. Using a dropping funnel, 3-chloropropyltrichlorosilane (CPTCS) was added dropwise over the course of 15 minutes. No temperature rise could be observed. Following the addition, stirring was continued for 15 minutes, after which the temperature of the oil bath was raised to 150° C. In the course of the subsequent stirring, the evolution of gas (HCl gas) was observable. A wash bottle filled with NaOH+water was used, with a slight underpressure, to neutralize HCl. Stirring was continued for 3.5 hours.

Distillation

The oil bath was heated to 85° C. (pressure to <1 mbar, cold trap, with dry ice and isopropanol to about −80° C.) and volatile constituents were taken off using a rotary evaporator. This was followed by stirring for 1 hour. Toluene was removed almost completely. The product obtained is solid and white.

Final mass: Carboxysilane: 181.2 g

NMR Analysis of the Carboxysilane (Test Report No. A090023426)

The $^1$H and $^{13}$C NMR spectra show the reaction product of chloro-propyltrichlorosilane with fatty acids. The chlorine atoms on the silicon were replaced, while the chloropropyl radical remains unchanged. Correspondingly, there are fractions of excess free acid present.

$^{29}$Si NMR Spectrum 74.5% Si silane (carboxysilane)

24.2% Si M structures (derived from carboxysilane)

1.3% Si D structures (derived from carboxysilane)

Chloride determination: Additionally, a chloride determination was carried out on the carboxysilane prepared.

TABLE 44

Chloride determination

| Determination | Result | Unit |
|---|---|---|
| Total chloride | 2.9 | % (mass) |

Solubility Investigation in Solvent

TABLE 45

| Solubility | Solubility |
|---|---|
|  | Vinyltrimethoxysilane (VTMO) |
| Carboxysilane | <1% |

A solid, white propylcarboxysilane of the three different fatty acids was prepared.

Summary of the Results of Examples 1 to 4:

TABLE 46

| Starting silane | Chain length of the fatty acids | Appearance |
|---|---|---|
| VTC | =<C14 | liquid (slightly viscous) slightly yellow |
|  | >=C14 | solid, white |
| PTCS | =<C14 | liquid (slightly viscous) slightly yellow |
|  | >=C14 | solid, white |
| SiCl4 | =<C14 | liquid (slightly viscous) slightly yellow |
|  | >=C14 | solid, white |
|  | C8, C16, C18, C22 | solid, white |
| CPTCS | =<C14 | liquid (slightly viscous) slightly yellow |
|  | >=C14 | solid, white |

Carboxysilanes with three to four different carboxyl radicals were successfully prepared. In the crude carboxysilane there is 5%-20% of free fatty acid present, which may result from the formation of dimers and trimers. In the case of CPTCS, however, it was not possible for the chlorine of the propyl group to be substituted.

SiCl$_4$ was synthesized with 3 long-chain fatty acids and one short-chain fatty acid. The short-chain fatty acid was unable overall to exert any influence over the consistency of the silicon carboxysilane. A white, solid product was obtained.

In the case of the from three or four different fatty acids with $R^{1(1a\ to\ d)}$ less than or equal to $R^1 \leq C14$ (carboxyl radicals=<C14), such as caprylic acid, capric acid, lauric acid, myristic acid, liquid carboxysilanes were isolated which dissolve readily in vinyltrimethoxysilane (carboxysilanes: slightly yellow, slightly viscous, and dissolve readily in VTMO >500).

The carboxysilanes prepared from three or four different fatty acids with $R^{1(1a\ to\ d)}$ greater than or equal to $R^1 \geq 14$ C atoms (carboxyl radicals>=C 14), such as myristic acid, stearic acid, palmitic acid, behenic acid, were solid, white products obtained, which dissolve poorly in VTMO (in VTMO 1%).

Without being tied to a theory, it is assumed that when three out of four of the carboxyl groups have more than 14 C atoms, the carboxysilanes prepared are solid, even if one of them has 14 C atoms or fewer (below 13 C atoms).

Use examples: Carboxysilanes as catalyst precursor compounds in Sioplas processes (as cat. MB)

Procedure: Extrusion

Grafting of PE-HD MG9641S from Borealis (M 56/77/08) with Vinyltrimethoxysilane in about 90% Form with Peroxide and Processing Assistant Grafting took place on the ZE 25 extruder from Berstorff. In the experiments, extrudates were produced. The grafted extrudates were pelletized following extrusion. Immediately after pelletizing, the pellets were packed into PE-Al-PE bags and welded. Prior to welding, the pellets were blanketed with nitrogen.

Processing Parameters of the Grafting Reaction on the ZE 25
Temperature profile: –/150/160/200/200/210/210/210° C.,
Rotary speed: about 100 rpm
Addition: 1.5 phr vinyltrimethoxysilane 90% form (addit. peroxide, processing assistant)
Kneading Operations: Preparation of the Masterbatches Masterbatches with catalyst were prepared. Processing took place on a Haake laboratory kneading apparatus. 49.0 g of PE were kneaded with 1.0 g of catalyst.

Processing Parameters

Kneading apparatus, filling hopper, belt die, belt take-off; filled intake zone,
Rotary speed: 30 rpm, temperature profile: 200° C./5 min
Production of Ready-Made Mixture of 95% PE-HD Vinyl-Silane Grafted with 5% Masterbatch (Cat. MB)

A mixture of 95% of PE-HD silane grafted with 5% of catalyst masterbatch (cat. MB) was subjected to kneading. Processing took place on a Haake laboratory kneading apparatus. The cat. MB contains 2% of the respective active ingredient in each case. The MBs of the invention contain a precursor compound or carboxysilane of the formula I and/or II. This was followed by compression molding at 200° C. to form plates, and, lastly, by crosslinking in a water bath at 80° C.

Processing Parameters:

Kneader, filling hopper; rotary speed: 30 rpm, temperature profile: 140° C./3 min; 2 min at 210° C.; 210° C./5 min; crosslinking time: 0 h, 4 h, and 22 h Results

TABLE 47

| Catalyst | from Ex.: | Gel [%] 0 h | Gel [%] 4 h at 80° C. water bath | Gel [%] 22 h at 80° C. water bath |
|---|---|---|---|---|
| VTC =< C14[1] | 1.1 | 31.6 | 38.8 | 53.3 |
| VTC >= C14[2] | 1.2 | 32.5 | 45.8 | 57.6 |
| PTCS =< C14[1] | 2.1 | 27.2 | 37.9 | 47.3 |
| PTCS >= C14[2] | 2.2 | 25.3 | 40.1 | 58.2 |
| SiCl4 =< C14[3] | 3.1 | 28.2 | 31.5 | 48.9 |
| SiCl4 >= C14[4] | 3.2 | 18.4 | 31.3 | 51.0 |
| CPTCS =< C14[3] | 4.1 | 24.2 | 40.0 | 49.3 |
| SiCl4 < C14 +> C14[5] | 3.3 | 35.0 | 41.2 | 56.2 |
| VTC + palmitic acid | Compar. Ex. | 16.96 | 32.94 | 46.21 |
| VTC + capric acid | Compar. Ex. | 22.48 | 35.82 | 45.68 |
| Tegokat 216 (DOTL) | | 44.12 | 61.37 | 65.79 |
| Blank value | | 12.51 | 16.43 | 33.60 |

[1]=<C14 carboxyl radicals: myristic acid, lauric acid, caprylic acid
[2]>=C14 carboxyl radicals: myristic acid, stearic acid, palmitic acid
[3]=<C14 carboxyl radicals: myristic acid, lauric acid, caprylic acid, capric acid
[4]=<C14 carboxyl radicals: myristic acid, stearic acid, palmitic acid, behenic acid
[5]SiCl4 < C14 +> C14 carboxyl radicals: caprylic acid, palmitic acid, behenic acid FIG. 1: shows an overview of the gel contents of the different carboxysilanes with three to four different fatty acid radicals, [95% PE-HD vinyl-silane grafted with 5% masterbatch/crosslinking in water bath at 80° C.

Figure 2:
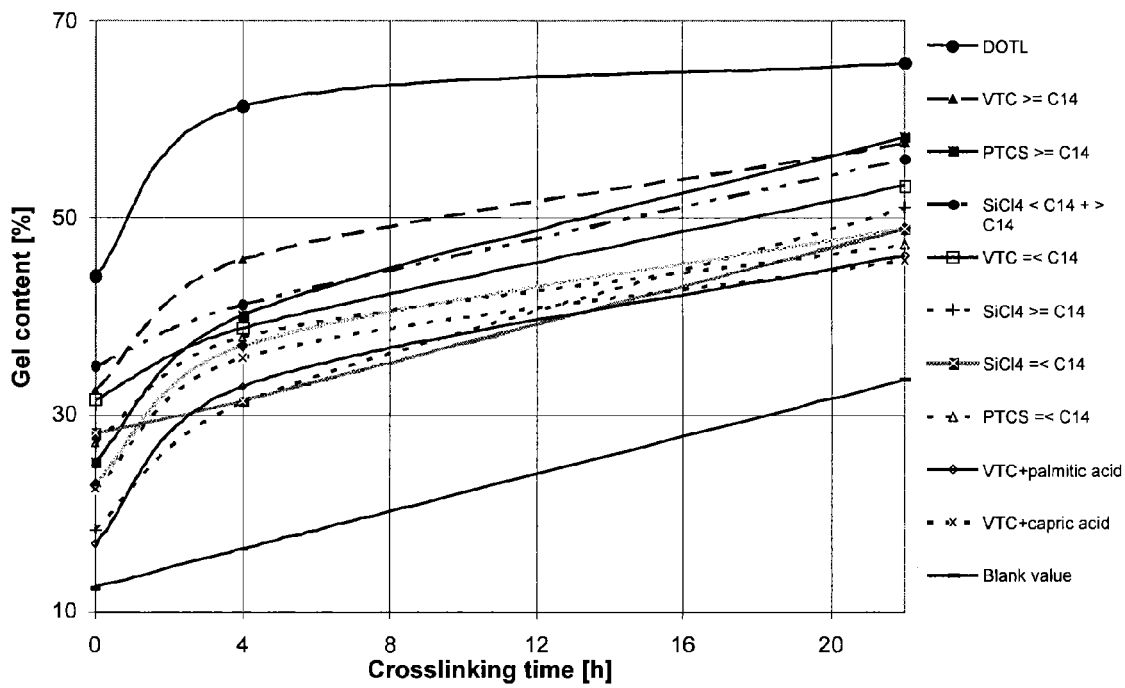

FIG. 2: shows a comparison of the carboxysilanes of the invention with different carboxyl radicals on the silane with the carboxysilanes which contain three or four identical carboxyl radicals.

Overall it can be stated that the carboxysilanes of the invention have catalyzed the crosslinking. The solid carboxysilanes, with carboxyl radicals greater than 14 C atoms, crosslink more effectively on average than the liquid carboxysilanes (carboxyl radicals smaller than 14 C atoms) and also better than the fatty acids and carboxysilanes with three identical carboxyl radicals.

The carboxysilanes synthesized with CPTCS were not included in the evaluation since it was not possible to substitute fatty acid for chlorine on the propyl in the course of the synthesis.

In comparison to the DOTL batch, the crosslinking rate and also the crosslinking of the carboxysilanes was lower. This can be attributed to the overdosing of the DOTL.

The invention claimed is:

1. A composition comprising:
   at least one carboxy-functionalized, silicon-containing precursor of two different organic acids, the precursor compound comprising: two carboxyl groups functionalized with different hydrocarbon radicals,
   wherein the precursor compound is of formula I, is an oligomeric siloxane of formula II derived from a compound of formula I, or is a mixture thereof:

$(A)_z SiR^2_x (OR^1)_{4-(z+x)}$ (I)

$(R^1O)[(R^1O)_{2-(x+z)}(R^2)_x Si(A)_z O]_a [Si(A)_z (R^2)_x (OR^1)_{2-(x+z)} O]_b R^1$ (II), wherein
   each z is independently 0, 1, or 2,
   each x is independently 0, 1 or 2,
   each (z+x) is less than or equal to 2,
   each A is independently an unsubstituted or substituted hydrocarbon group,
   each $R^1$ is independently at least two carbonyl-$R^3$ groups,
   each $R^3$ is independently a substituted or unsubstituted hydrocarbon radical having 3 to 45 C atoms,
   each $R^2$ is independently a linear, branched, or cyclic alkyl group having 1 to 24 C atoms, or an aryl group,
   a is greater than or equal to 1, and
   b is greater than or equal to 1.

2. The composition of claim 1, wherein each A is independently a linear, branched, or cyclic alkyl-, alkenyl-, aryl-, alkylaryl-, arylalkylene-, cycloalkenyl-alkylene-, haloalkyl-, or acryloyloxyalkyl-functional group.

3. The composition of claim 1,
   wherein either:
   (i) each z is 1; each x is 0; each A is independently a linear, branched, or cyclic alkyl, alkenyl or haloalkyl group having 1 to 8 C atoms or a cyclohexenyl-ethylene group; each $R^1$ is independently two or three different carbonyl-$R^3$ groups; and each $R^3$ is independently an unsubstituted hydrocarbon radical having 3 to 45 C atoms,
   or
   (ii) each z is 0; each x is 0; each $R^1$ is independently two, three, or four different carbonyl-$R^3$ groups; and each $R^3$ is independently an unsubstituted hydrocarbon radical having 3 to 45 C atoms.

4. The composition of claim 1, wherein
   each $R^1$ is independently at least two different carbonyl-$R^3$ groups,
   a first $R^3$ group is an unsubstituted hydrocarbon radical having 3 to 14 C atoms, and
   another $R^3$ group is an unsubstituted hydrocarbon radical having 15 to 45 C atoms.

5. The composition of claim 1,
   wherein the composition is liquid from about 10° C. to 80° C.

6. The composition of claim 1, wherein the precursor compound has a solubility of greater than 40% in a hydrocarbon-functionalized alkoxysilane or siloxane.

7. The composition of claim 1,
   wherein the precursor compound comprises a compound of formula I, and optionally an oligomeric compound of formula II, and wherein either:

(iii) z is 1; A is H$_3$C(CH$_2$)$_2$—, H$_2$C=CH$_2$—, ClCH$_2$(CH$_2$)$_2$—, C$_6$H$_9$—(CH$_2$)$_2$—, 3-C$_6$H$_9$—(CH$_2$)$_2$—, 2-C$_6$H$_9$—(CH$_2$)$_2$—, 1-C$_6$H$_9$—(CH$_2$)$_2$—, C$_6$H$_8$—(CH$_2$)$_2$—, 1,3-C$_6$H$_8$—(CH$_2$)$_2$—, or 2,4-C$_6$H$_8$—(CH$_2$)$_2$—; OR$^1$ in formula I comprises two or three different radicals R$^1$ that are each independently —COC$_7$H$_{15}$, —COC$_9$H$_{19}$, —COC$_{11}$H$_{23}$, —COC$_{13}$H$_{27}$, —COC$_{15}$H$_{31}$, —COC$_{17}$H$_{35}$, or —COC$_{21}$H$_{43}$; or (iv) z is 0 and OR$^1$ in formula I comprises two, three, or four different radicals R$^1$ that are each independently —COC$_7$H$_{15}$, —COC$_9$H$_{19}$, —COC$_{11}$H$_{23}$, —COC$_{13}$H$_{27}$, —COC$_{15}$H$_{31}$, —COC$_{17}$H$_{35}$, or —COC$_{21}$H$_{43}$.

8. The composition of claim 1,
wherein the precursor compound comprises at least two carboxyl groups functionalized with different hydrocarbon radicals, and is obtained by a process comprising reacting a halosilane of formula III:

$$(A)_z SiR^2_x (Hal)_{4-(z+x)} \quad (III)$$

with at least two different organic acids of the formula IV:

$$HOR^1 \quad (IV),$$

wherein
z is 0, 1, or 2,
x is 0, 1, or 2,
(x+z) is less than or equal to 2,
each Hal is independently a halogen that is chlorine or bromine, and a molar ratio of the at least two different organic acids to the halogen groups is at least stoichiometric.

9. The composition of claim 1,
wherein the precursor compound comprises at least one selected from the group consisting of a compound of formula I and a corresponding oligomeric compound thereof;
the compound of formula I is selected from the group consisting of:
H$_3$C(CH$_2$)$_2$—Si(OCOC$_7$H$_{15}$)$_p$(OCOC$_{11}$H$_{23}$)$_p$(OCOC$_{13}$H$_{27}$)$_p$,
H$_3$C(CH$_2$)$_2$—Si(OCOC$_{13}$H$_{27}$)$_p$(OCOC$_{15}$H$_{31}$)$_p$(OCOC$_{17}$H$_{35}$)$_p$,
H$_2$C=CH$_2$—Si(OCOC$_7$H$_{15}$)$_p$(OCOC$_{11}$H$_{23}$)$_p$(OCOC$_{13}$H$_{27}$)$_p$,
H$_2$C=CH$_2$—Si(OCOC$_{13}$H$_{27}$)$_p$(OCOC$_{15}$H$_{31}$)$_p$(OCOC$_{17}$H$_{35}$)$_p$,
C$_6$H$_9$—(CH$_2$)$_2$—Si(OCOC$_7$H$_{15}$)$_p$(OCOC$_{11}$H$_{23}$)$_p$(OCOC$_{13}$H$_{27}$)$_p$,
C$_6$H$_9$—(CH$_2$)$_2$—Si(OCOC$_{13}$H$_{27}$)$_p$(OCOC$_{15}$H$_{31}$)$_p$(OCOC$_{17}$H$_{35}$)$_p$,
ClCH$_2$(CH$_2$)$_2$—Si(OCOC$_7$H$_{15}$)$_p$(OCOC$_{11}$H$_{23}$)$_p$(OCOC$_{13}$H$_{27}$)$_p$,
ClCH$_2$(CH$_2$)$_2$—Si(OCOC$_{13}$H$_{27}$)$_p$(OCOC$_{15}$H$_{31}$)$_p$(OCOC$_{17}$H$_{35}$)$_p$,
(H$_{19}$C$_9$OCO)$_p$(ClCH$_2$(CH$_2$)$_2$)Si(OCOC$_7$H$_{15}$)$_p$(OCOC$_{11}$H$_{23}$)$_p$(OCOC$_{13}$H$_{27}$)$_p$,
(H$_{43}$C$_{21}$OCO)$_p$(ClCH$_2$(CH$_2$)$_2$Si(OCOC$_{13}$H$_{27}$)$_p$(OCOC$_{15}$H$_{31}$)$_p$(OCOC$_{17}$H$_{35}$)$_p$,
(H$_{19}$C$_9$OCO)$_p$(ClCH$_2$(CH$_2$)$_2$)Si(OCOC$_7$H$_{15}$)$_p$(OCOC$_{11}$H$_{23}$)$_p$(OCOC$_{13}$H$_{27}$)$_p$,
(H$_{19}$C$_9$OCO)$_p$Si(OCOC$_7$H$_{15}$)$_p$(OCOC$_{11}$H$_{23}$)$_p$(OCOC$_{13}$H$_{27}$)$_p$,
(H$_{43}$C$_{21}$OCO)$_p$Si(OCOC$_{13}$H$_{27}$)$_p$(OCOC$_{15}$H$_{31}$)$_p$(OCOC$_{17}$H$_{35}$)$_p$,
(H$_{33}$C$_{16}$)—Si(OCOC$_7$H$_{15}$)$_p$(OCOC$_{11}$H$_{23}$)$_p$(OCOC$_{13}$H$_{27}$)$_p$,
(H$_{33}$C$_{16}$)—Si(OCOC$_{13}$H$_{27}$)$_p$(OCOC$_{15}$H$_{31}$)$_p$(OCOC$_{17}$H$_{35}$)$_p$,
(H$_{17}$C$_8$)—Si(OCOC$_7$H$_{15}$)$_p$(OCOC$_{11}$H$_{23}$)$_p$(OCOC$_{13}$H$_{27}$)$_p$,
(H$_{17}$C$_8$)—Si(OCOC$_{13}$H$_{27}$)$_p$(OCOC$_{15}$H$_{31}$)$_p$(OCOC$_{17}$H$_{35}$)$_p$,
(H$_9$C$_4$)—Si(OCOC$_7$H$_{15}$)$_p$(OCOC$_{11}$H$_{23}$)$_p$(OCOC$_{13}$H$_{27}$)$_p$, and
(H$_9$C$_4$)—Si(OCOC$_{13}$H$_{27}$)$_p$(OCOC$_{15}$H$_{31}$)$_p$(OCOC$_{17}$H$_{35}$)$_p$;

each p is independently 0, 1, 2, or 3, with the proviso that p is 1 for at least two different carboxyl groups;
a sum of all ps per precursor compound is 3 if z in formula I is 1; and
a sum of all ps is 4 if the precursor compound is a tetracarboxy-functionalized precursor compound of formula I and if z=0.

10. A carrier material, comprising the composition of claim 1.

11. The composition of claim 1, further comprising:
an organofunctional silane compound of formula V:

$$(B)_b SiR^4_c (OR^5)_{3-d-c} \quad (V)$$

wherein each d is independently 0, 1, 2, or 3,
each c is independently 0, 1, 2, or 3,
each sum c+d is less than or equal to 3,
each B is independently a monovalent unsaturated hydrocarbon group, each R$^7$ independently is a hydrogen atom, a methyl group, or a phenyl group, E is —CH$_2$—, —(CH$_2$)$_2$—, —(CH$_2$)$_3$—, —O(O)C(CH$_2$)$_3$— or —C(O)O—(CH$_2$)$_3$—,
q is 0 or 1,
each R$^5$ independently is methyl, ethyl, n-propyl, or iso-propyl,
each R$^4$ independently is a substituted or unsubstituted hydrocarbon group.

12. A carboxy-functionalized, silicon-containing precursor compound of two different organic acids, the precursor compound comprising: two carboxyl groups functionalized with different hydrocarbon radicals,
wherein the precursor compound is of formula I, is an oligomeric siloxane of formula II derived from a compound of formula I, or is a mixture thereof:

$$(A)_z SiR^2_x (OR^1)_{4-(z+x)} \quad (I)$$

$$(R^1 O)[(R^1 O)_{2-(x+z)}(R^2)_x Si(A)_z O]_a [Si(A)_z (R^2)_x (OR^1)_{2-(x+z)} O]_b R^1 \quad (II),$$

each z is independently 0, 1, or 2,
each x is independently 0, 1 or 2,
each (z+x) is less than or equal to 2,
each A is independently an unsubstituted or substituted hydrocarbon group,
each R$^1$ is independently at least two carbonyl-R$^3$ groups,
each R$^3$ is independently a substituted or unsubstituted hydrocarbon radical having 3 to 45 C atoms,
each R$^2$ is independently a linear, branched, or cyclic alkyl group having 1 to 24 C atoms, or an aryl group,
a is greater than or equal to 1, and
b is greater than or equal to 1.

13. A masterbatch, comprising:
the precursor compound of claim 12;
a thermoplastic base polymer, a silane-grafted base polymer, a silane-copolymerized base polymer, a monomer of a thermoplastic base polymer, a monomer of a silane-grafted base polymer, a monomer of a silane-copolymerized base polymer, a prepolymer of a thermoplastic base polymer, a prepolymer of a silane-grafted base polymer, a prepolymer of a silane-copolymerized base polymer, or a mixture thereof; and optionally a radical initiator.

14. The composition of claim 8, wherein:

x is 0, and z is 0 or 1.

15. The composition of claim 1, further comprising:

a radical initiator, wherein the composition is suitable for crosslinking thermoplastic base polymers.

\* \* \* \* \*